(12) United States Patent
Hussan et al.

(10) Patent No.: US 8,738,299 B2
(45) Date of Patent: May 27, 2014

(54) GENE FINDING USING ORDERED SETS OF DISTINCT MARKER STRINGS

(75) Inventors: Jagir R. Hussan, Tamil Nadu (IN); Albee Jhoney, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 1492 days.

(21) Appl. No.: 11/534,439

(22) Filed: Sep. 22, 2006

(65) Prior Publication Data

US 2007/0128631 A1 Jun. 7, 2007

Related U.S. Application Data

(62) Division of application No. 10/324,509, filed on Dec. 20, 2002, now Pat. No. 7,158,889.

(51) Int. Cl.
| | |
|---|---|
| *G06G 7/58* | (2006.01) |
| *G01N 31/00* | (2006.01) |
| *G01N 33/48* | (2006.01) |
| *G01N 33/50* | (2006.01) |
| *G06F 19/22* | (2011.01) |
| *G06F 19/12* | (2011.01) |

(52) U.S. Cl.
CPC .............. *G06F 19/22* (2013.01); *G06F 19/12* (2013.01)
USPC .................... 702/20; 702/19; 702/27; 703/11

(58) Field of Classification Search
None
See application file for complete search history.

(56) References Cited

U.S. PATENT DOCUMENTS

| | | | |
|---|---|---|---|
| 5,844,094 A * | 12/1998 | Hudson et al. | ............. 530/387.3 |
| 7,158,889 B2 | 1/2007 | Hussan et al. | |
| 2004/0121332 A1 | 6/2004 | Hussan et al. | |

FOREIGN PATENT DOCUMENTS

WO      WO 99/66302      12/1999

OTHER PUBLICATIONS

Craig et al. Ordering of cosmid clones covering the Herpes simplex virus type I (HSV-I) genome: a test case for fingerprinting by hybridisation. Nucleic Acids Research, vol. 18, 1990, pp. 2653-2660.*

Zweig SE. Analysis of large nucleic acid dot matrices on small computers. Nucleic Acids Research, vol. 12, 1984, pp. 767-776.*

(Continued)

*Primary Examiner* — Russell S Negin
(74) *Attorney, Agent, or Firm* — Schmeiser, Olsen & Watts, LLP; John Pivnichny

(57) ABSTRACT

A method and system for finding in a DNA sequence, a gene represented by an ordered set of marker strings is disclosed. Sub-strings in the DNA sequence matching each marker string are identified. In a set ordered via occurrence of the marker strings in the ordered set of marker strings, the score and position of each sub-string whose score satisfies a matching constraint is recorded. For each except the last marker string, directed links are created between each identified sub-string that matches the marker string and any identified sub-strings that match the subsequent marker string, subject to the directed links satisfying an inter-marker length constraint. Traced are all paths that connect each identified sub-string that matches the first marker string to an identified sub-string that matches the last marker string using the directed links. The paths satisfy a sequence length constraint and are stored in memory of a computer system.

21 Claims, 14 Drawing Sheets

(56) References Cited

OTHER PUBLICATIONS

Rosefeld, Azriel; Parallel String Parsing Using Lattice Graphs; May 1981; TR-1036, AFOSR-77-3271; Computer Vision Laboratory, Computer Science Center, University of Maryland, College Park, MD 20742.

Burge, et al.; Prediction of Complete Gene Structures in Human Genomic DNA; J. Mol. Biol. ( 1997); 268; Academic Press Limited; pp. 78-94.

Gelfand, et al.; Gene recognition via spliced sequence alignment; Proc. Natl. Acad. Sci. USA; vol. 93; Aug. 1996; Genetics; pp. 9061-9066.

Spang, et al.; Statistics of large-scale sequence searching; Bioinformatics; vol. 14, No. 3; 1998; Oxford University Press; pp. 279-284.

Karlin, et al.; Applications and statistics for multiple high-scoring segments in molecular sequences; Proc. Natl. Acad. Sci. USA; vol. 90; Jun. 1993; Evolution; pp. 5873-5877.

Karlin, et al.; Methods for assessing the statistical significance of molecular sequence features by using general scoring schemes; Proc. Natl. Acad. Sci. USA; vol. 87; Mar. 1990; Evolution; pp. 2264-2268.

Yu, et al.; Statistical Significance of Probabilistic Sequence Alignment and Related Local Hidden Markov Models; Journal of Computational Biology; vol. 8, No. 3; 2001; Mary Ann Liebert, Inc.; pp. 249-282.

Shamir, Ron; Algorithms for Molecular Biology; Dec. 11, 2000; Lecture 7; Fall Semester, 2001; Tel Aviv University; 27 pages.

Notice of Allowance (Mail Date Aug. 30, 2006) for U.S. Appl. No. 10/324,509, filed Dec. 20, 2002, First Named Inventor Jagir R. Hussan.

Office Action (Mail Date Jul. 28, 2006) for U.S. Appl. No. 10/324,509, filed Dec. 20, 2002, First Named Inventor Jagir R. Hussan.

Office Action (Mail Date Jul. 11, 2006) for U.S. Appl. No. 10/324,509, filed Dec. 20, 2002, First Named Inventor Jagir R. Hussan.

Office Action (Mail Date Feb. 16, 2006) for U.S. Appl. No. 10/324,509, filed Dec. 20, 2002, First Named Inventor Jagir R. Hussan.

Office Action (Mail Date Aug. 23, 2006) for U.S. Appl. No. 10/324,509, filed Dec. 20, 2002, First Named Inventor Jagir R. Hussan.

* cited by examiner

GENE FINDING USING ORDERED SETS OF DISTINCT MARKER STRINGS

This application is a divisional of Ser. No. 10/324,509, filed Dec. 20, 2002 now U.S. Pat. No. 7,158,889.

FIELD OF THE INVENTION

The present invention relates to finding sequences using ordered sets and more particularly to finding genes in DNA sequences.

BACKGROUND

Gene expression is a biological process by which a DNA sequence generates a protein. The process involves two steps, namely transcription and translation. Transcription produces a messenger RNA (mRNA) sequence using the DNA sequence as a template. The subsequent process, called translation, synthesizes the protein according to information coded in the mRNA. In eukaryotes (higher organisms), the region of the DNA coding for a protein is usually not continuous but comprises alternating stretches of introns (non-coding parts) and exons (coding parts that result in the production of a part of the protein). Six reading frames exist, of which only one contains the gene sequence. Hence, genes cannot generally be read directly from a DNA sequence.

There are more than 3 billion bases of human DNA sequences. In the human genome, only 2%-3% of the sequences comprise coding. As a consequence of the size of the database, manual searching for genes that code for proteins is not practical. A need thus exists for an automated method of finding genes.

Chris Burge and Samuel Karlin, in a paper entitled "*Prediction of Complete Gene Structures in Human Genomic DNA*", Journal of Molecular Biology (1997) 268, pp. 78-94, discuss a probabilistic method to predict sequences which code for proteins (i.e. find gene sequences). However, this method is not optimised for finding a specific gene.

Mikhail S. Gelfand, Andrey A. Mimov, and Pavel A. Pevzner, in a paper entitled "*Gene Recognition via Spliced Sequence Alignment*", Proceedings National Academy of Science (USA), August 1996, Volume 93, pp. 9061-9066, present a technique of finding high scoring blocks. The blocks are then combined to form a sequence, the weight of which is the optimal alignment score of the sequence with the target sequence. The blocks can be combined in many ways and the complexity of the problem increases with the number of blocks. Moreover, the second stage of finding the optimal alignment score increases the time required for completion of the algorithm. The technique does not take into account the presence of synonyms and consequent effects on the alignment scores.

International Patent Publication No. WO/9966302, published on 23 Dec. 1999, by the MUSC Foundation for Research and Development, and entitled "*Recognition of Protein Coding Regions in Genomic DNA Sequences*", describes the use of neural networks to identify coding regions. Disadvantages associated with neural networks include the time necessary to train a network and the fact that information is stored in a form that is not easily understood by humans, restricts further analysis. In applications where target marker strings change rapidly, neural networks are not the best choice, given the time and effort required in training (both positive and negative samples are necessary).

Ron Shamir, in a lecture handout entitled "*Algorithms for Molecular Biology*", Lecture 7, Tel Aviv University, dated "Fall Semester 2001", discusses general concepts and algorithms relating to gene finding.

Rainer Sprang and Martin Vingron, in a paper entitled "*Statistics of Large-Scale Sequence Searching*", published in Bioinformatics, Volume 14, No. 3, 1998, pp 279-284, discuss the statistical significance of scores in the context of a database search.

Samuel Karlin and Stephen F. Altschul, in a paper entitled "*Methods for assessing the statistical significance of molecular sequence features by using general scoring schemes*", Proceedings of the National Academy of Science (USA), March 1990, Volume 87, pp. 2264-2268, present a theory that provides precise numerical formulas for assessing the statistical significance of any region in a sequence with a high aggregate score. The object is to identify whether particular sequence patterns occur simply by chance.

In another paper entitled "*Applications and statistics for multiple high-scoring segments in molecular sequences*", Proceedings of the National Academy of Science (USA), June 1993, Volume 90, pp. 5873-5877, Samuel Karlin and Stephen F. Altschul discuss score-based measures of molecular sequence features as an aid in the study of proteins and DNA. In particular, the paper discusses potential problems encountered when using score-based techniques to identify similar sequences.

In a paper entitled "*Statistical Significance of Probabilistic Sequence Alignment and Related Local Hidden Markov Models*" and published in the Journal of Computational Biology, Vol. 8, No. 3, 2001, pp 249-282, Yi-Kuo Yu and Terence Hwa propose a modified "semi-probabilistic" alignment consisting of a hybrid of the Smith-Waterman alignment. Specifically, the proposed method uses Hidden Markov Models to predict coding regions, rather than automaton's, profiles and scores for matching.

SUMMARY

Aspects of the present invention provide a method, a system and a computer program product for identifying occurrences of a sequence of ordered marker strings in a string are disclosed. The method includes the steps of identifying sub-strings in the string that match the marker string, creating directed links between a sub-string that matches a particular marker string and all the sub-strings that match a subsequent marker string in the ordered sequence of marker strings, and identifying occurrences of the sequence in the string by tracing one or more corresponding paths from each sub-string that matches the first marker string to all sub-strings that match the last marker string by following the directed links.

Further aspects of the present invention provide a method, a system and a computer program product for finding a gene in a DNA sequence. The method includes the steps of identifying sub-strings in the DNA sequence that match a marker string, recording, in a set ordered according to the occurrence of the marker strings in the gene, the score and position of each sub-string whose score satisfies a matching constraint, creating directed links between each recorded sub-string that matches the marker string and any recorded sub-strings that match the subsequent marker string in the ordered sequence of marker strings subject to the directed links satisfying an inter-marker length constraint, and tracing all paths that connect each recorded sub-string that matches the first marker string in the ordered set of marker strings to a recorded sub-string that matches the last marker string in the ordered set of marker strings using the directed links, wherein the paths satisfy a sequence length constraint.

The step of identifying sub-strings in the DNA sequence that match a marker string preferably include the sub-steps of generating a score representative of the degree of match between a marker string and a sub-string of the DNA sequence using a profile corresponding to the marker string, and identifying the match subject to the score satisfying a predetermined constraint. The profile can be representative of a set of strings that are considered matches of the marker string and/or a set of strings that are considered mismatches of the marker string.

The directed links preferably satisfy an inter-marker length constraint that comprises one of a minimum number of characters between sub-strings that match successive marker strings in the DNA sequence, a maximum number of characters between sub-strings that match successive marker strings in the DNA sequence, and a predetermined number of characters between sub-strings that match successive marker strings in the DNA sequence.

The step of tracing all paths that connect each recorded sub-string that matches the first marker string in the ordered set of marker strings to a recorded sub-string that matches the last marker string in the ordered set of marker strings preferably includes the sub-steps of selecting a sub-string corresponding to a marker string, tracing all possible forward paths from each occurrence of the sub-string to all sub-strings that match the first marker string, tracing all possible backward paths from each occurrence of the sub-string to all sub-strings that match the last marker string, and building complete paths between sub-strings that match the first marker string and sub-strings that match the last marker string, wherein the complete paths comprise the forward paths and the backward paths. Furthermore, the step of building complete paths preferably includes the sub-steps of individually de-normalizing path information relating to the forward and backward paths.

Preferably, the complete paths satisfy a sequence length constraint that comprises one of a minimum number of characters, a maximum number of characters and a predetermined number of characters.

Further, preferably, the sum of the scores of the sub-strings comprising each complete path is within a predetermined tolerance of a desired path score, the desired path score comprising the sum of the highest scores recorded in respect of each marker string.

BRIEF DESCRIPTION OF THE DRAWINGS

Features and preferred embodiments of the present invention are described hereinafter, by way of example only, with reference to the accompanying drawings in which.

DETAILED DESCRIPTION

A method, a system and a computer program product have been described for for identifying one or more occurrences of a sequence of ordered marker strings in a string. The preferred method, computer system and computer program product are described with specific reference to "the gene finding problem". However, it is not intended that the present invention be so limited as the principles thereof have general applicability to numerous fields and applications. For example, the present invention has application to the protein matching problem, wherein the set <G> corresponds to protein domains and the target string S comprises a protein database. Alternatively, the set <G> corresponds to protein domains and the target string S comprises a newly sequenced protein whose function/similarity/homology is required. Other applications include but are not limited to:

- the creation of reliable document signatures in the field of Natural Language Processing/Machine Learning;
- the creation of adaptive human machine interfaces in the field of machine intelligence to construct systems that can work in noisy environments and with incomplete and/or incoherent data (e.g. a system to help patients in shock or extremely senile persons, etc.); and
- adaptive machine vision systems to enable systems to identify objects whose features evolve or change (not dramatically) with time.

A Statement of the General Problem

Given:
- a string S of length $\gamma$, belonging to the alphabet $\Sigma$;
- an ordered set M of marker strings, each of length $l_i$ and belonging to the alphabet $\Sigma' \subset \Sigma$ such that $m_i, m_j \in M$ (i<j implies that end $m_i$<start of $\overline{m_j}$);
- an ordered set P of profiles, wherein:
    each profile $p_i \in P$ is a $l_i \times k_i$ matrix,
    $p_i$ corresponds to $m_i$ of set M,
    $k_i$ is the length of $m_i$, and
    $l_i$ is the number of elements in $\Sigma'_i$;
- an ordered set $S_w$ of normalized scores wherein:
    each $s_i \in S_w$, corresponds to $m_i \in M$;
- an automaton, which can recognize all the words in the language formed by $\{\Sigma, Gr\}$, wherein Gr comprises a grammar corresponding to the alphabet $\Sigma$;
- a global sequence length L;
- a global inter-$m_i$ length $\alpha$ and tolerance level T, (0<T<1), defining the range of similarity to be addressed.

Figure 1A:
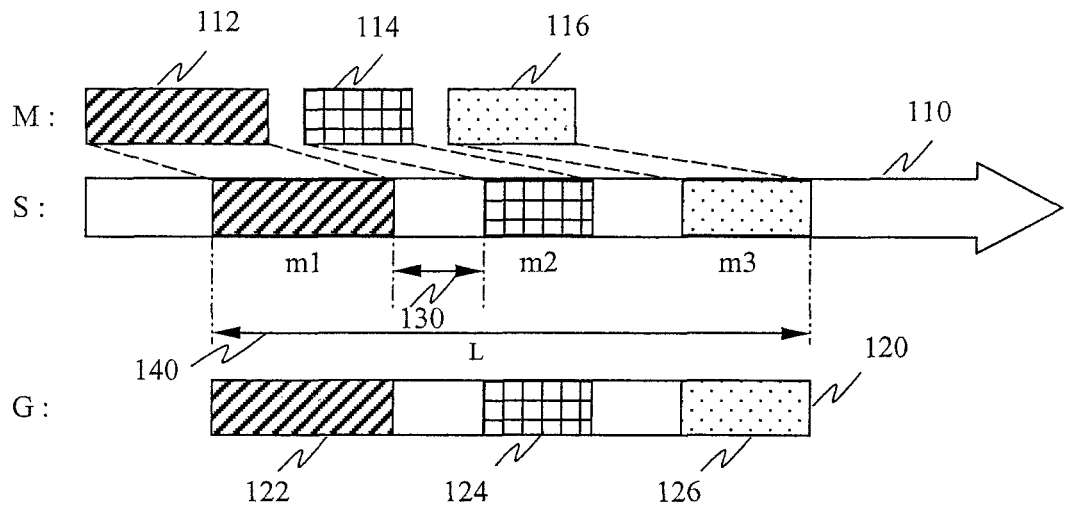
FIG. 1A is a diagrammatic representation of the general problem.

Referring now to FIG. 1A, the problem can be stated as follows:

Find sequences <G> 120 in string S 110 such that all $m_i$ 112, 114 ... 116∈M occur in the order they had been in the set M, such that the following constraints are satisfied:

A. Inter-Marker Length Constraint
1. Length between the strings $m_i$, $m_{i+1}$ is less than $\alpha$ 130, or
2. Length between the strings $m_i$, $m_{i+1}$ is equal to $\alpha$ 130, or
3. Length between the strings $m_i$, $m_{i+1}$ is greater than $\alpha$ 130.

B. Sequence Length Constraint
1. Length of G 120 is less than L 140; or
2. Length of G 120 is equal to L 140; or
3. Length of G 120 is greater than L 140.

The resultant sequences <G> should be positive samples and should be found within an acceptable response time. The choice of inequality for each of constraints A and B is determined by the target application.

Assumptions made in the input data sets are as follows:
1. The language formed by {$\Sigma$, Gr} may contain synonyms;
2. The string S may contain insertions, deletions and substitutions of any length, which can occur anywhere and any number of times.

The Gene Finding Problem

In the gene finding problem described hereinbefore, the string S corresponds to a DNA sequence. The coding region for a gene is preceded by certain other regions called initiators and promoters, which play an important role in the identification of the coding region and in the expression of the gene. The end of a coding region is also indicated by a sequence made of terminating codons. Within the coding region, the introns and exons alternate. All these regions, in their order of occurrence, form the set M of marker strings.

Mutations and environmental factors can cause a coding region to be coded in more than one form. The various possible codes that exist and the distribution thereof can be determined by analyzing a large number of samples. This information can be represented in the form of a matrix of sequence logos or elements similar to sequence logos. The profiles P correspond to these matrices.

The function provided by a protein depends on the structure of that protein, which is dependent on the amino acid sequence, which is determined by the sequence of nucleotides (the gene sequence). More than one gene sequence can code for a single function. It is believed that if there is a 30% similarity in two sequences, that there would be significant similarity in their structure and function. Sequences can be categorized based on the similarity of the function that they provide. Comparison between sequences can be performed using a matching function that statistically determines a match/mismatch score. All sequences that have a match/mismatch score above/below the determined score can be declared to belong to a particular category. The set $S_w$ of weights corresponds to these scores.

An amino acid can be coded by more than one codon. Thus, synonyms exit and an automaton can be used to recognize such in order to take them into account.

A genome is spread over chromosomes. Each chromosome is responsible for the expression of certain genes and hence certain functions. Gene coding regions do not cross chromosome boundaries and a coding region's length is constrained by the fact that a longer coding region is relatively more susceptible to a large number of mutations and errors can be introduced during replication, etc. Thus, by examining a large number of genes, one can arrive at a length within which all the coding regions' lengths lie. This is the global sequence length parameter L.

Similar restrictions apply for coding regions in that an exon for a gene cannot be found in another chromosome, nor can an exon for a gene cross the terminating region (an exon that crosses a terminating region doesn't belong to the gene). Thus, similarly to the gene sequence length, an inter-exon (promoter-initiator, initiator-exon exon-exon, exon-terminating sequence) length can be determined. This is referred to as $\alpha$.

The DNA is a large chunk of information that usually contains repetitious regions. It has been observed that only a part of the DNA codes for genes, thus creating the possibility of obtaining matches to random sequences. This could sometimes undermine the choice of genuine sequences that may not score higher than such random sequences. In order to minimize these effects, a tolerance level T is created and all those sequences that fall within the tolerance level are considered. The choice of the tolerance level T determines the number of elements in the final result set.

An Outline of a Solution to the General Problem

The solution comprises three main steps, namely:
STEP A: Locate the matching segments $m_i$ in S,
STEP B: Identify all the possible sequence sets, and
STEP C: Identify the optimal sequence set.

Figure 2:
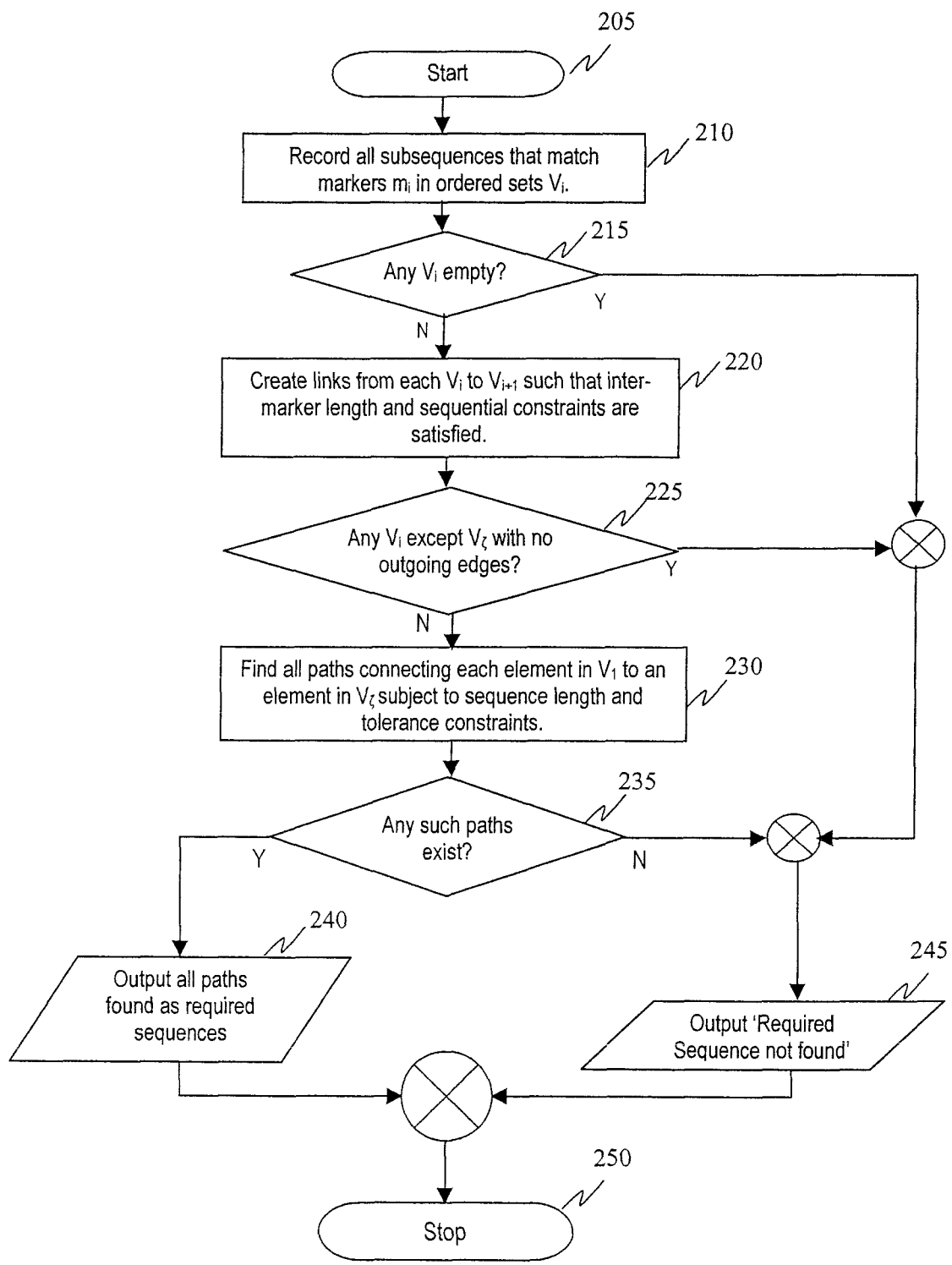
FIG. 2 is a flowchart of an algorithm for solving the general problem, according to an embodiment of the present invention.

FIG. 2 is a flowchart of an algorithm of a solution to the general problem, wherein step 210 corresponds to STEP A, step 220 corresponds to STEP B and step 230 corresponds to STEP C.

Figure 1B:
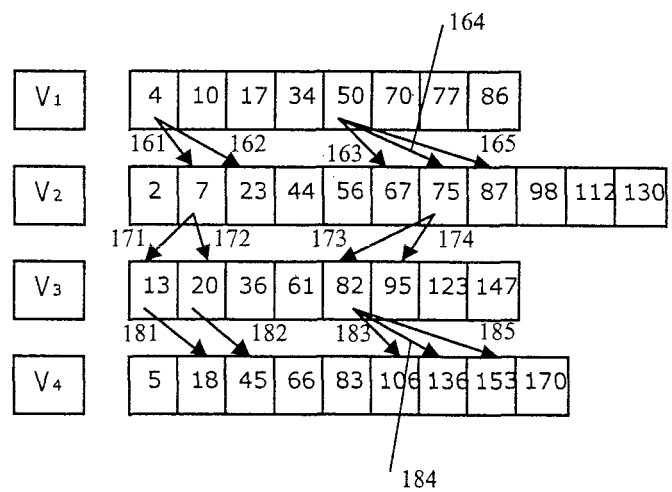
FIG. 1B is a diagrammatic representation showing sequence sets identified according to an embodiment of the present invention.

At step 210, all sub-sequences occurring in the target string S that match the marker strings $m_i \epsilon M$, are found using the profiles $p_i$. The matching sub-sequences are required to satisfy a constraint that their mismatch score is less than $s_i$ or that their match score is greater than $s_i$. The position of occurrence and score of each match is recorded in the set $V_i$, which is ordered on the position of occurrence of the matching sub-sequences in S. FIG. 1B shows an example comprising sets $V_1$ to $V_4$ containing information relating to the ordered positions of occurrence of matches of the marker strings $m_1$ to $m_4$, respectively. For example, matches for marker string $m_1$ occur at positions 4, 10, 17, 34, 50, 70, 77 and 86 in string S.

If no matches are found for a marker string $m_i$ at step 215, non-existence of the sub-sequence is announced at step 245 and the algorithm is terminated at step 250.

At step 220, all possible sequence sets are located. Directed links (arcs) are created between elements in $V_i$ and $V_{i+1}$, such that inter-marker length constraint and the condition that $v_i.\text{end} < v_j.\text{start}$ (where $v_i \epsilon V_i$ and $v_j \epsilon V_{i+1}$) are satisfied. Step 220 is performed for each $V_i$ generated in step 210, except for $V_\zeta$ corresponding to string $m_\zeta$, where $m_\zeta$ is the marker string occurring last in the ordered set M. Step 220 results in a graph $\Omega$ that has multiple source and sink points. The example in FIG. 1B shows directed links 161 to 165 between elements in $V_1$ and $V_2$, directed links 171 to 174 between elements in $V_2$ and $V_3$ and directed links 181 to 185 between elements in $V_3$ and $V_4$. As can be seen, the constraint that $v_i.\text{end} < v_j.\text{start}$ (i<j) is satisfied for each directed link.

If no links can be created for any $V_i$, $V_{i+1}$ at step 225 (where 1<i<$\zeta$ and $\zeta$ is the number of elements in M), non-existence of the sequence is announced at step 245 and the algorithm is terminated at step 250.

At step 230, all paths that connect an element $v_1$ in $V_1$ to an element v in $V_\zeta$ (where $V_\zeta$ is the matching set for the last marker $m_\zeta$ in M), such that all the paths from the graph $\Omega$ satisfy a sequence length constraint and their score is within a tolerance level T of the expected best path's score, are identified. The pair ($v_1$, $v_\zeta$) represents an instance of the sequence G on the string S. Referring to the example in FIG. 1B, paths that connect an element in $V_1$ to an element in $V_4$ include directed links {161, 171, 181}, {161, 172, 182}, {164, 173, 183}, {164, 173, 184} and {164, 173, 185}.

If any paths exist that satisfy both the sequence length and tolerance constraints, and no more such paths can be found, at step 235, the paths are returned as <G> (existences of the sequence G on the string S) at step 240 and the algorithm is terminated at step 250.

If no such paths exist, at step 235, non-existence of the sequence is announced at step 245 and the algorithm is terminated at step 250.

A Detailed Solution of the General Problem

This section provides additional detail relating to the steps of the foregoing outline of a solution to the general problem.

Step A: Locate the Matching Segments $m_i$ in S

For each string $m_i \in M$, matches on the target string S are identified. Starting with $S_0$ and comparing $S_0 \ldots S_{k-1}$ (where $k=l_i$), the profile information $p_i$ is used in the matching process to allow substitutions. Matching continues with $S_1 \ldots S_k$ upto $S\gamma_{-k-1} \ldots S\gamma$. During matching, a holistic/polynomial function is used to give a match/mismatch score for each match that is generated, so that the matches can be ranked based on closeness to the target string. The starting position and score of each match are recorded in an ordered set V such that, for all $v_i, v_j \in V$, $v_i.\text{start} < v_j.\text{start}$ ($i<j$). If $vs_{max}$ denotes the score of the highest scoring element(s) in V, any elements added to the set V should have a match score of greater than $vs_{max}*(1-T)$. Alternatively, if $vs_{min}$ denotes the score of the lowest scoring element(s) in V, any elements added to the set V should have a mismatch score of less than $vs_{max}*(1+T)$. The foregoing condition is called the set existence condition. If $vs_{max}$ changes when an element is added, all elements that do not satisfy the set existence condition are removed from the set V, either when the change occurs or at the end of the matching process. If V is empty when matching for a $m_i$ is complete, the required sequence G does not exist and the algorithm is terminated.

Figure 3:
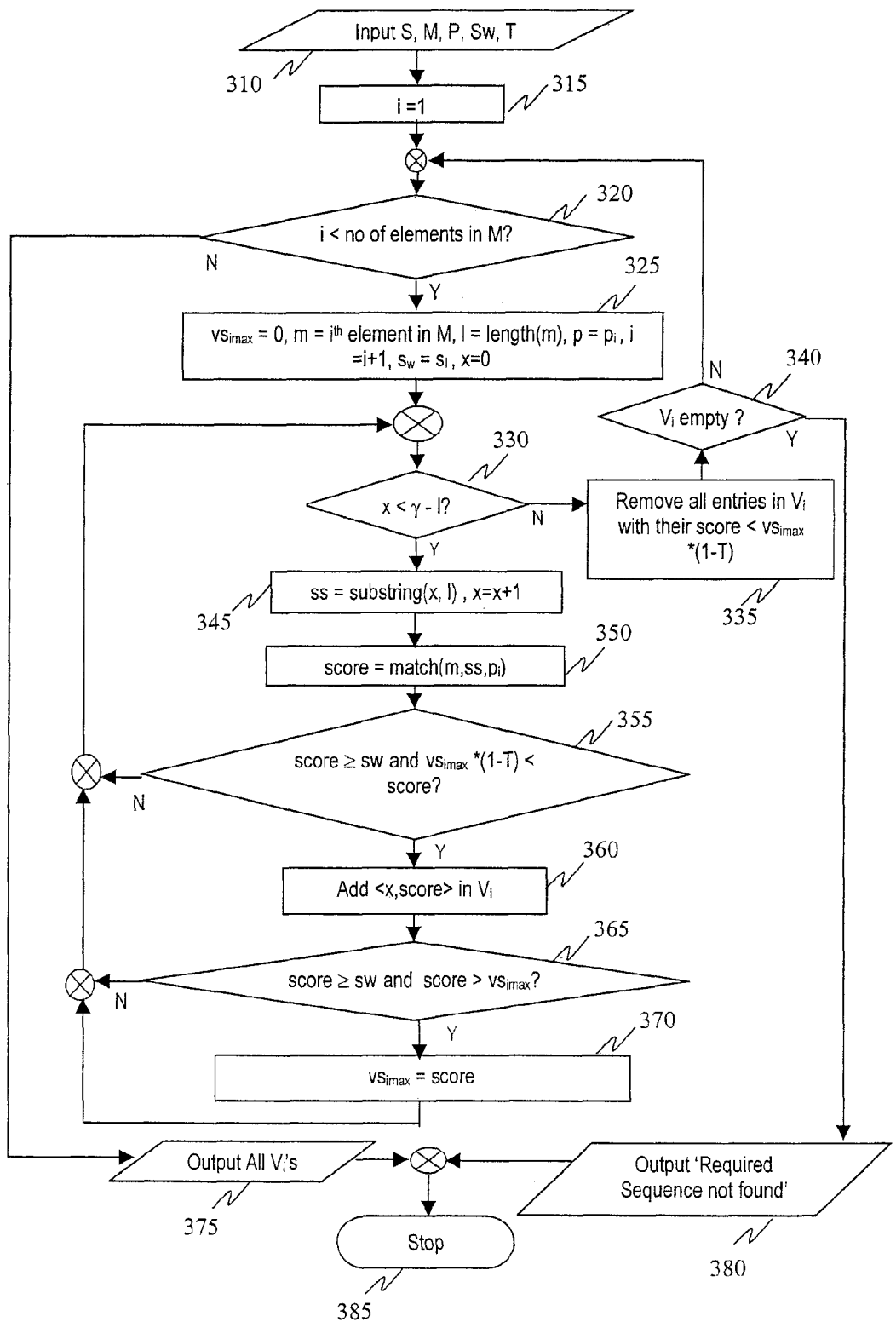
FIG. 3 is a flowchart that provides additional detail of step 210 of FIG. 2.

FIG. 3 is a flowchart of a process to find segments or sub-strings of the string S that match any of the marker strings M. FIG. 3 thus provides additional detail of step 210 of FIG. 2.

The string S, the set of marker strings M, the set of profiles P (corresponding to the set of marker strings M), the set of weights $S_w$ and a tolerance value T, are inputs at step 310.

Matching is performed for each marker string $m_i$ using the loop variable i, which is initialized at step 315, tested at step 320 and incremented at step 325. Variables relating to a specific marker string are initialized at step 325.

The variable x, which is initialized at step 325, tested at step 330 and incremented at step 345, is used to select each subsequent sub-string from string S for matching against a current marker string $m_i$.

If a further sub-string of S that corresponds in length to the current marker string $m_i$ exists, at step 330, the sub-string is selected at step 345. At step 350, a matching score is determined for the sub-string selected in step 345 against the current marker string $m_i$.

Step 355 tests whether the score determined in step 355 is at least equal to an expected weighted score and is within a specified tolerance of the previous maximum score for set $V_i$ (i.e. $vs_{max}*(1-T)$). If so, the score is added to the ordered set $V_i$ at step 360. If not, processing returns to step 330.

Step 365 determines whether the score determined in step 355 is at least equal to the expected weighted score and is higher than the current maximum score for set $V_i$. If so, the current score is stored as the maximum score at step 370. Processing then returns to step 330.

If no further sub-strings of S that correspond in length to the current marker string $m_i$ exist, at step 330, then entries in the set $V_i$ whose score is not within the specified tolerance of the maximum score for set $V_i$ (i.e. $vs_{max}*(1-T)$) are removed, at step 335. If the set $V_i$ is empty, at step 340, it is output that the required sequence was not found and the process terminates at step 385. If there are additional elements in the set $V_i$, processing returns to step 320.

Once the string S has been searched for sub-strings corresponding to each of the marker strings $m_i$, the sets $V_i$ are output at step 375 and the process terminates at step 385.

Table 1, hereinafter, contains pseudo-code for a process to find segments or sub-strings of the string S that match any of the marker strings M.

TABLE 1

For each $m_i \in M$
    Initialize $vs_{imax}$ with 0, since the match score is of interest
    $l_i$ = length($m_i$)
    p = $p_i$
    For x = 0 to $\gamma - l_i$
        SS = $S_x S_{x+1} \ldots S_{x+li-1}$
        score = match(m, SS, p), /* a string matching function
        that returns the
            similarity between strings a & b, based on the profile
            information p */
        If score ≥ $s_i$ and $vs_{imax}*(1-T)$ < score then
            Add <x,score> to $V_i$
        If score ≥ $s_i$ and score > $vs_{imax}$ then
            $vs_{imax}$ = score
    End For /* For x = 0 to $\gamma - l_i$*/
    For each $v_i \in V_i$
        If $vs_{imax}*(1-T) > v_i.\text{score}$ then
            Remove $v_i$ from $V_i$
    End For
    If $V_i$ = { } then
        Return failure
    Add $V_i$ to V
End For /* For each $m_i \in M$*/

It should be noted that both FIG. 3 and Table 1 make use of a 'match score', as opposed to a 'mismatch score'. Appropriate changes will need to be made for the case of a 'mismatch score', as will be understood by an appropriately skilled person.

Step B: Identify all the Possible Sequence Sets.

The output from STEP A comprises the ordered sets $V_1$, $V_2 \ldots V_m$, where m is number of elements in M. Accordingly, $V_i$ denotes the ordered set V corresponding to the marker string $m_i$ and $V_\zeta$ denotes the ordered set V for the last marker string ($m_\zeta$) of the ordered set M.

Directed links (arcs) are created between all elements in $V_i$ and $V_{i+1}$ that satisfy an inter-marker length constraint and the condition that $v_i.\text{end} < v_j.\text{start}$ (where $v_i \in V_i$ and $v_j \in V_{i+1}$). If there exists any set $V_i$ except $V_\zeta$, with a zero arc count, the algorithm is terminated. This condition occurs when no sequence with elements of M occurring in that order exists in S.

The output of STEP B provides a graph $\Omega$ populated with nodes and edges that represents all the possible sequence sets. The graph $\Omega$ is a layered graph, with each layer representing an element in the marker set M.

Figure 4:
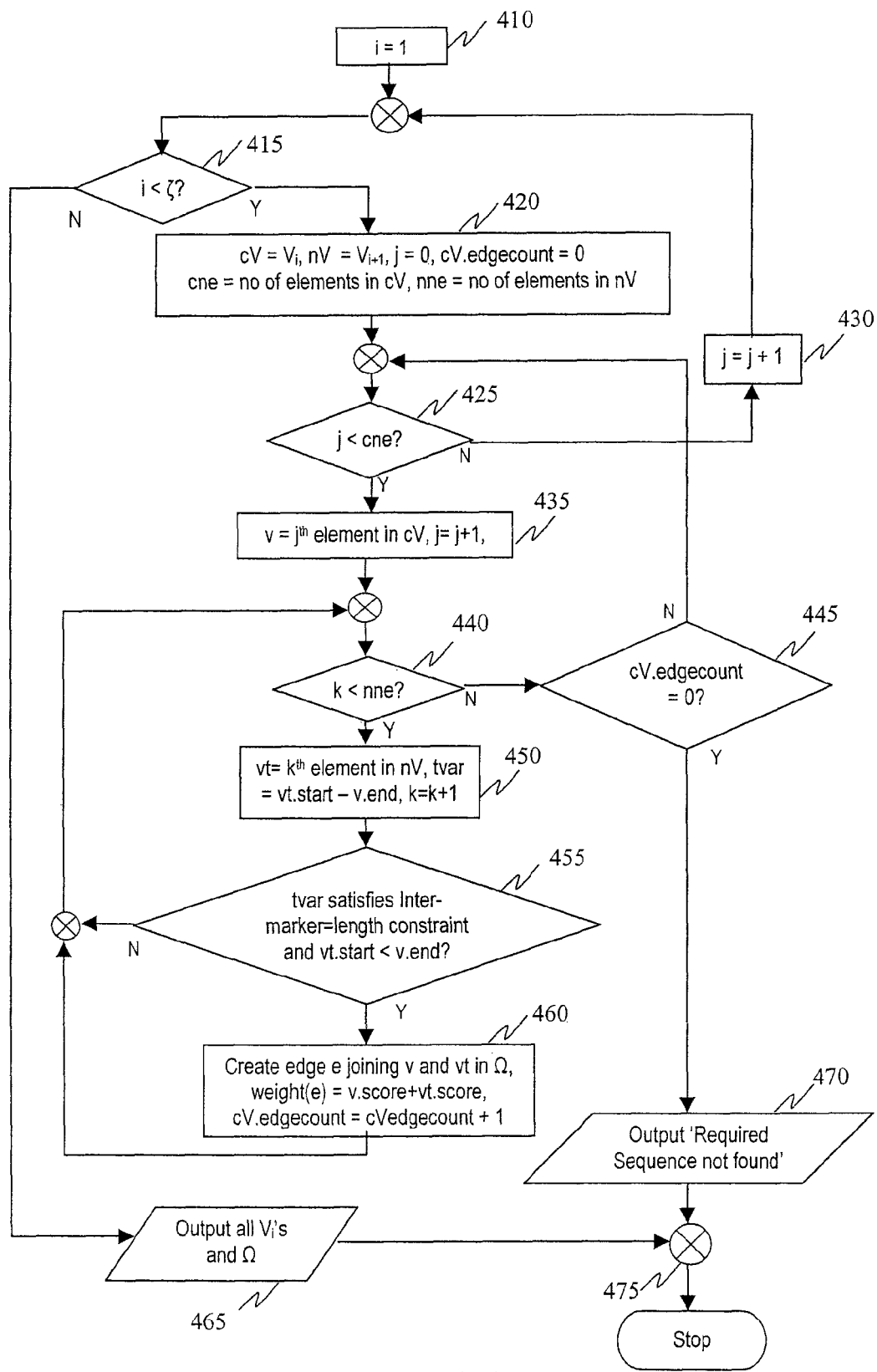
FIG. 4 is a flowchart that provides additional detail of step 220 of FIG. 2.

FIG. 4 is a flowchart of a process to identify all the possible sequence sets of sub-strings in string S that match marker strings $m_i$. FIG. 4 provides additional detail of step 220 of FIG. 2.

The process is performed for each pair of adjacent sets $V_i$ and $V_{i+1}$ using the loop variables i and k, respectively. The loop variable i is initialized at step 410, tested at step 415 and incremented at step 435.

At step 420, sets $V_i$ and $V_{i+1}$ are selected, a counter (edge-count) is initialized for counting the number of edges or directed links and the number of elements in sets $V_i$ and $V_{i+1}$ are determined.

If all the elements of the set $V_i$ have been processed, at step 425, the loop variable i is incremented at step 430 and processing returns to step 415. If, on the other hand, more elements of the set $V_i$ are still to be processed, at step 425, the loop variable i is incremented and another loop variable k is initialized to zero at step 435.

If the loop variable k is equal to the number of elements in set $V_{i+1}$ (i.e. processing of set $V_i$ is complete) and the edgecount value for set $V_i$ is zero, at step 445, processing returns to step 425. If the edgecount value for set $V_i$ is not zero, at step 445, it is output that no required sequences were found at step 470 and the process terminates at step 475. If the loop variable k is less than the number of elements in set $V_{i+1}$, at step 440, the loop variable k is incremented and the difference in position between the $k^{th}$ element in set $V_{i+1}$ and the $i^{th}$ element in the set $V_i$ (in the string S) is determined and stored in the variable tvar, at step 450.

If the value of tvar satisfies the inter-marker length constraint and the start position of the element in set Vi+1 is after the end position of the element in set Vi, at step 455, an edge e is created that joins the $i^{th}$ element in $V_i$ and the $k^{th}$ element in $V_{i+1}$, at step 460. The weight of edge e is set to the sum of the scores of the $i^{th}$ element in $V_i$ and the $k^{th}$ element in $V_{i+1}$ and the edgecount variable is incremented, also at step 460. Processing then continues at step 440.

Once each set $V_i$, except for the last set $V_\zeta$, has been processed to determine the presence of directed links to set $V_{i+1}$, at step 415, the sequence sets are output at step 465 and the process terminates at step 475.

Table 2, hereinafter, contains pseudo-code for a process to identify all the possible sequence sets.

TABLE 2

```
For each V_i except for V_ζ
    Let cV = V_i
    Let nV = V_{i+1}
    For each element v_i of cV
        For each element v_j of nV
            if v_j.start - v_i.end satisfies Mean inter-marker length
            constraint and v_i.end < v_j.start then
                Create an directed arc e joining v_i and v_j in Ω
                weight(e) = v_i.score + v_j.score
                Add One to the arc count of ordered set V_i
            End If
        End For
    End For
```

Step C: Identify the Optimal Sequence Set.

The input to STEP C is a graph $\Omega$ that represents all possible sequences and the output of STEP C is the optimal sequence set <G>.

Figure 5:
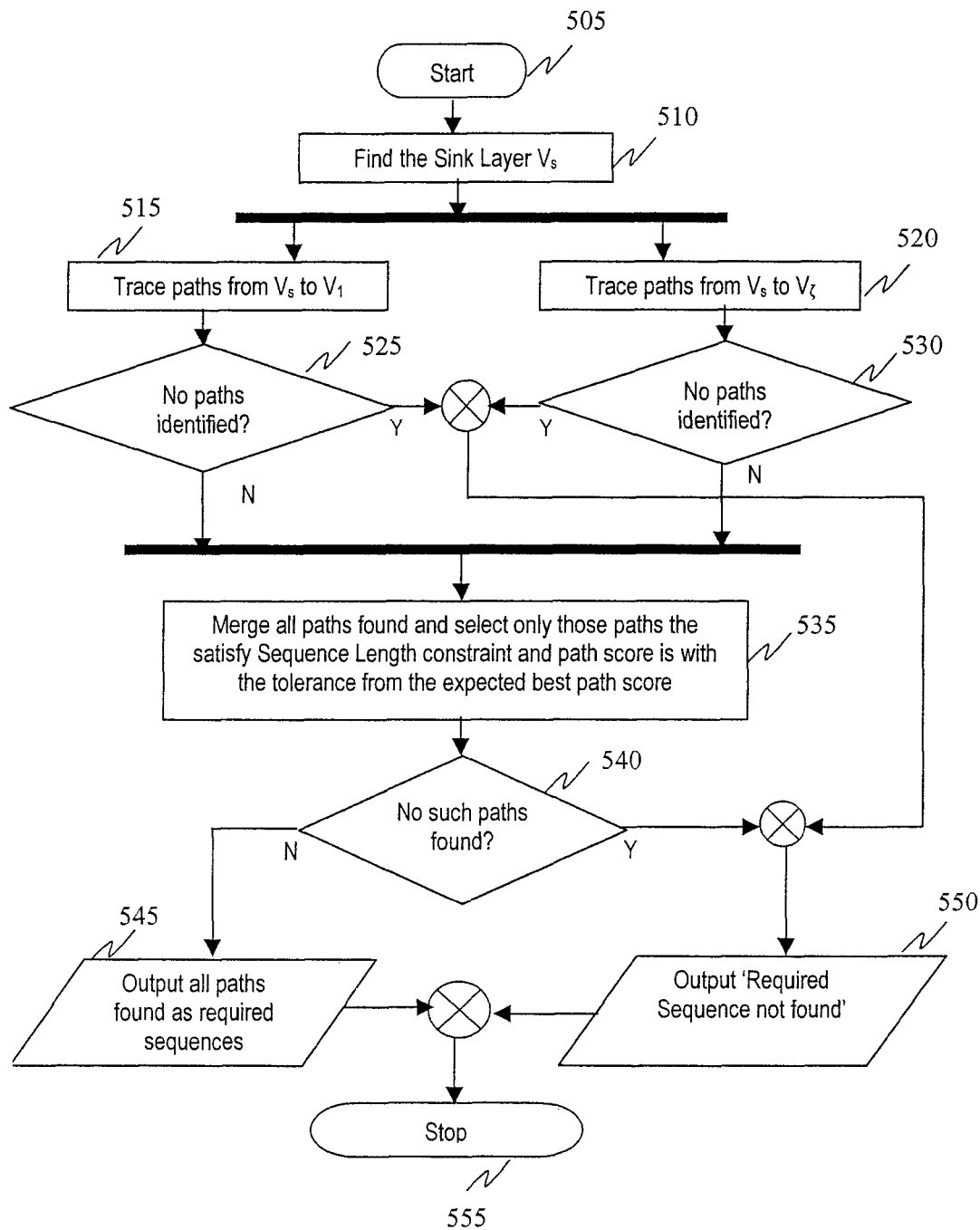
FIG. 5 is a flowchart that provides additional detail of step 230 of FIG. 2.

FIG. 5 is a flowchart of a process to identify the optimal sequence set of sub-strings in string S that match marker strings $m_j$. FIG. 5 thus provides additional detail of step 230 of FIG. 2.

At step 510, the starting point X in the graph $\Omega$ is located. The layer containing the starting point X in the graph $\Omega$ is designated the sinklayer $V_s$.

The following heuristics can be applied to locating the starting point X in the graph $\Omega$:

Select the set $V_i$, which has the lowest arc count. If there exists more than one such set then compare the neighboring sets of each such set $(V_{i-1}, V_{i+1})$ and take the set whose neighboring set has the lowest edge count among the sets considered. If a choice cannot be made, take any random $V_i$ among the $V_i$'s.

Select the last set $V_\zeta$.

Among the V sets, select the set that has minimum number of $v_i$'s that are connected by an edge from the neighboring two sets. This method is much more involved but is guaranteed to produce better or equivalent results compared to the above two methods.

The paths from the sinklayer $V_s$ to the first layer $V_1$ of the graph $\Omega$ are traced at step 515. For each element $v_i$ of the sinklayer $V_s$ with at least one edge, paths that connect an element from the set in the sinklayer $V_s$ to an element in $V_1$, are traced. The sinklayer divides the match-ordered sets into two classes, one of which contains all the match-ordered sets $V_1$ through $V_s$ and the other of which contains all the match-ordered sets $V_s$ through $V_\zeta$. The output of this process is an array of nodes (the Forward Global Path Array) that form the forward path. The first element is from $V_1$, the second from $V_2, \ldots,$ and the last from $V_s$. If no paths are identified at step 525, it is output that the required sequence has not been found at step 550 and the process terminates at step 555.

The paths from the sinklayer $V_s$ to the last layer $V_\zeta$ of the graph $\Omega$ are traced at step 520. A modified version of the process described hereinbefore for step 515 is applied to the other set $V_s$ to $V_\zeta$, to generate a Backward Global Path Array. If no paths are identified at step 530, it is output that the required sequence has not been found at step 550 and the process terminates at step 555.

At step 535, the identified paths are merged (i.e., the Forward and Backward Global Path Arrays are combined) and subjected to sequence length and tolerance constraints to determine the optimal sequence set. The tolerance constraint requires that the score of a merged path is within an acceptable tolerance limit of the expected best path score. Any paths found that satisfy both constraints (tested at step 540) are output as required sequences at step 545, after which the process terminates at step 555. If no paths satisfy both of the constraints (tested at step 540), it is output that the required sequence has not been found at step 550, after which the process terminates at step 555.

Tracing a Path

A TracePathThread thread is created for each edge of the nodes in the sinklayer to trace a path. The thread is created with the following input state:

direction (set as forward), nextNodeIndex: The index of node from which the edge originates (next-node), nextNodeMatchOrderedSetNumber: The next node's match-ordered set number, nodeIndex: The input node's index, matchOrderedSetNumber: The input-node's match-ordered set number arrayOfInputNodes: An array with the input-node's index as the first element and all the elements from the input array of nodes in the order they have occurred in that input array. Note that this will be empty for each element in the sinklayer.

The output produced by the thread is the (direction) Global Path Array. The structure of each element in the array is as follows:

nextNodeIndex: The next-node index, nextNodeMatchOrderedSetNumber: The next-node's match-ordered-set-number, nodeIndex: The current-node index, matchOrderedSetNumber: The current-node's match ordered set number, and arrayofInputNodes: An array that contains indices of nodes that have been encountered upto the current node with the last node encountered as the first element.

Pseudo-code for the TracePathThread algorithm for constructing the Forward Global Path Array is contained in Table 4, hereinafter.

TABLE 4

TracePaththread : Each thread works in the following manner:
1) Read the node that has been input, call this input-node
The node from which the thread was created is called 'CurrentElement'
2) If the node has not been read by another thread
    Then
        2.a) Set the node-read indicator on /*to block the node from other threads*/
            Add inputNodeIndex to ArrayOfInputNodes
        2.b) For each out going edge (except one), create a TracePathThread thread to trace
            n–1 branches of the path.
            For the current path, add that node as the first element to the input array of
            nodes. Set input node value to next-node's value and input
            MatchOrderedSetNumber is updated to the next-node's match-ordered set
            number.
        2.b) Continue with Step 1.
    Else
        2.a) If the input-node belongs to target layer ($V_1$)
        Then (there would be no outgoing edges)
            Add the input-node as the first element to the array of input nodes.
            Make an entry in the Forward global path array with null for input-node's
            index, 0 for input node's MatchOrderedSetNumber and the input-node's
            index, input node's MatchOrderedSetNumber, ArrayOfInputNodes
            Exit
        Else (The input-node has been read)
            Make an entry in the Forward global path array with the input-node's index,
            input-node's match-ordered set number, CurrentElement's index,
            CurrentElement's MatchOrderedSetNumber and the ArrayOfInputNodes
            Exit.

Figure 6:
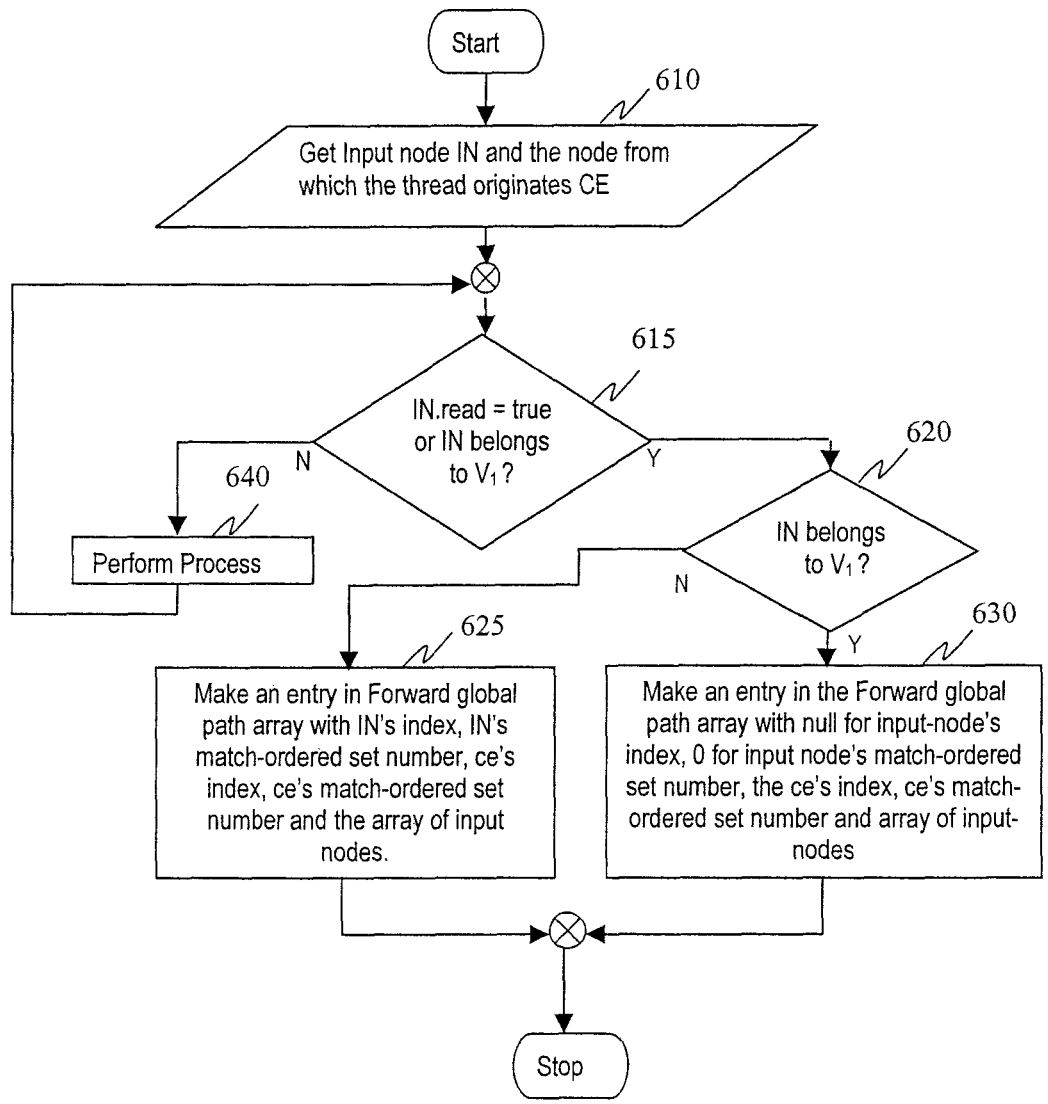
FIG. 6 is a flowchart that provides additional detail of step 515 of FIG. 5.
Figure 7:
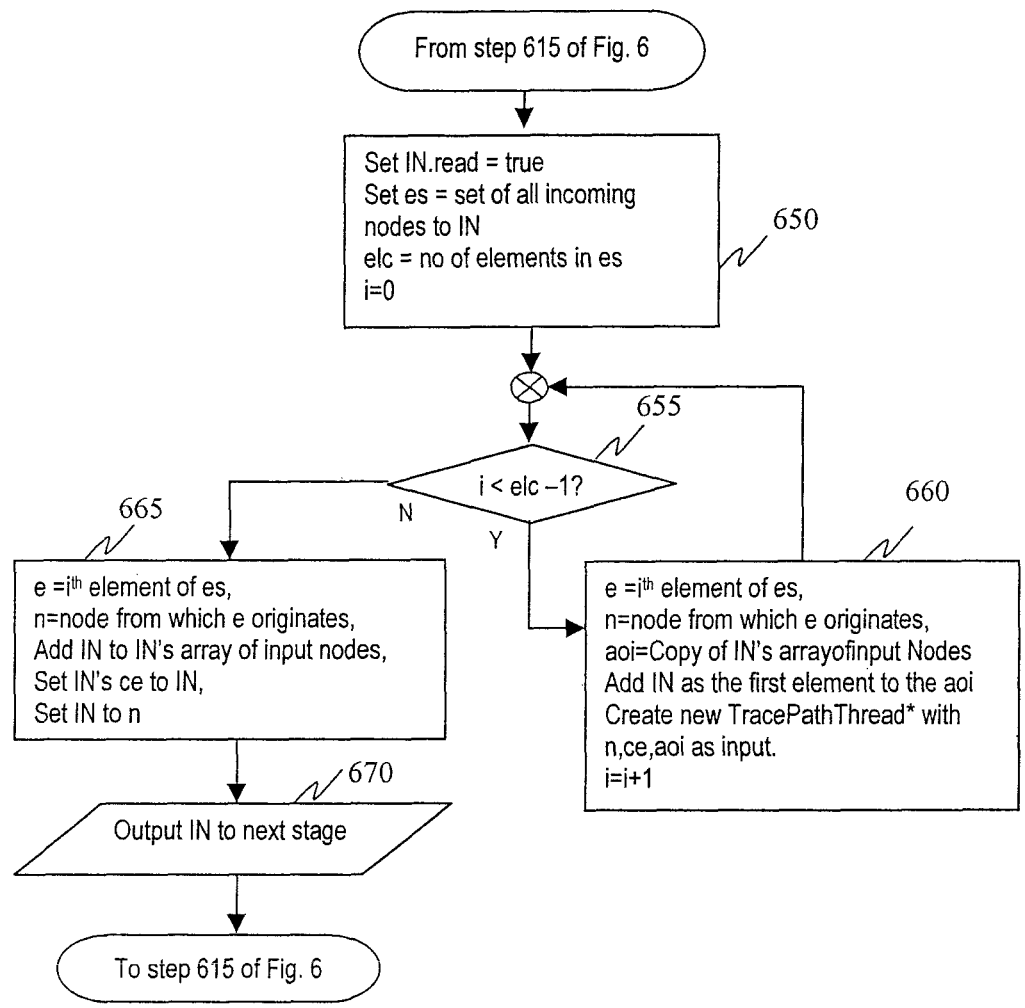
FIG. 7 is a flowchart that provides additional detail of step 640 of FIG. 6.

FIGS. 6 and 7 show additional detail of a process for tracing paths from the sinklayer $V_s$ to the first layer $V_1$ of the graph Ω (step 515 of FIG. 5).

At step 610, the input node IN and the node from which the thread originates (the current element) CE are read. At step 615, it is determined whether the input node IN has been read by another thread or whether the input node IN belongs to $V_1$. If not (N), processing continues at step 640, which is presented in further detail in FIG. 6B. If yes (Y) and the input node IN does not belong to $V_1$ (N), at step 620, an entry is made in the Forward Global Path Array (FGPA) at step 625. If yes (Y) and the input node IN does belong to $V_1$ (Y), at step 620, an entry is made in the FGPA at step 630. The process ends when an entry is made in the FGPA.

The entry made in the FGPA at step 625 includes the input node's index and match-ordered set number, the current element's index and match-ordered set number and the array of input nodes. Alternatively, the entry made in the FGPA at step 630 includes a null for the input node's index, zero for the input node's match-ordered set number, the current element's index and match-ordered set number and the array of input nodes.

FIG. 6B shows more detail of step 640 in FIG. 6A. At step 650, the node IN is set as having been read and some internal variables are initialized.

Step 655 ensures that each incoming node to node IN is processed at step 660, by comparing a loop variable i to the number of incoming nodes elc. When the last incoming node been processed (N), (i.e., i=elc−1), processing continues at step 665.

For each incoming node, at step 660, the incoming node is added as the first element to the array of incoming nodes and a new TracePathThread is created using three input parameters: the intermediate target node n, the intermediate source node ce and the array of nodes encountered from the source node to the intermediate source node. The array of nodes encountered from the source node to the intermediate source node corresponds to the array of input nodes from the previous stage. The next incoming node is selected using loop variable by incrementing loop variable i and processing continues at step 655.

When all the incoming nodes to node IN (elements of 'es') have been processed (N), at step 655, the input node IN is added as the first element to the array of incoming nodes and the current element CE is set to the input node IN at step 665. Then, also at step 665, the input node IN is set to the node 'n' from which the edge or link 'e' (i.e., the last element of 'es') originates. At step 670, the input node IN is output to the next stage of the process (i.e., step 615), which requires the variable IN as an input.

A similar process to that of FIGS. 6 and 7 can be performed to trace paths between the sinklayer $V_s$ and the last layer $V_ζ$ of the graph Ω (step 520 of FIG. 5), as will be understood by an appropriately skilled person. In this case, the target set is $V_ζ$ and the array produced is the Backward Global Path Array.

Building Complete Paths from the Forward and Backward Global Path Arrays

The Global Path Arrays contain the path information in a normalized form. An element of a Global Path Array contains a part of the path information and depends on other elements for the complete path. For example, an element may contain 'A-a-b-c', where 'A' denotes a reference to another element in the Global Path Array, which may contain 'd-e-f'. Complete path information 'd-e-f-a-b-c' can be extracted by substituting the relevant cross-references. Hence, complete paths are built by individually de-normalizing the Forward Global Path Array and the Backward Global Path Array.

Figure 8:
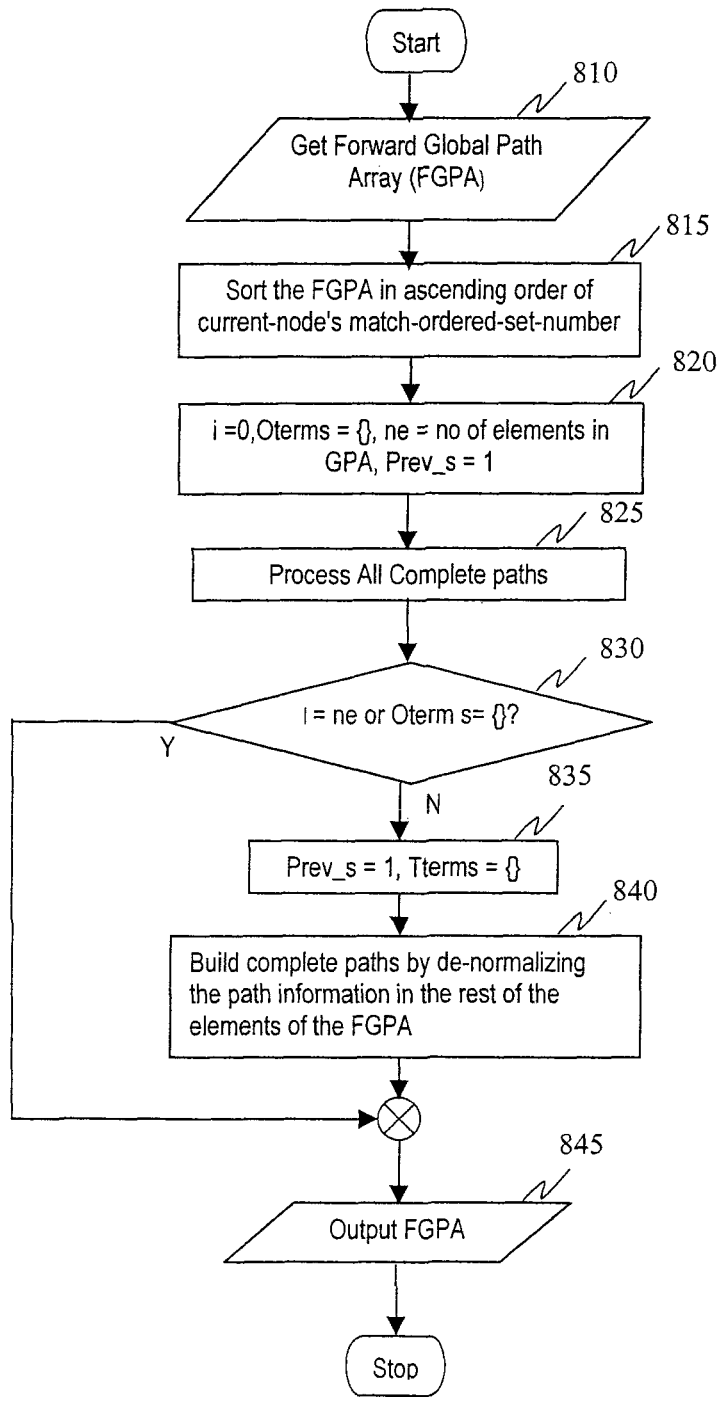
FIG. 8 is a flowchart for building complete paths from the Forward Global Path Array (FGPA)

FIG. 8 is a flowchart of a process to build complete paths in the forward direction, which provides additional detail of step 515 of FIG. 5. The output of this process is used by step 535 of FIG. 5.

The Forward Global Path Array (FGPA) is retrieved at step 810 and sorted in ascending order of the current node's match-ordered set number at step 815. Various internal variables are initialized at step 820, including setting the set Oterms to empty and the previous layer (Prev_s) to 1.

Figure 9:
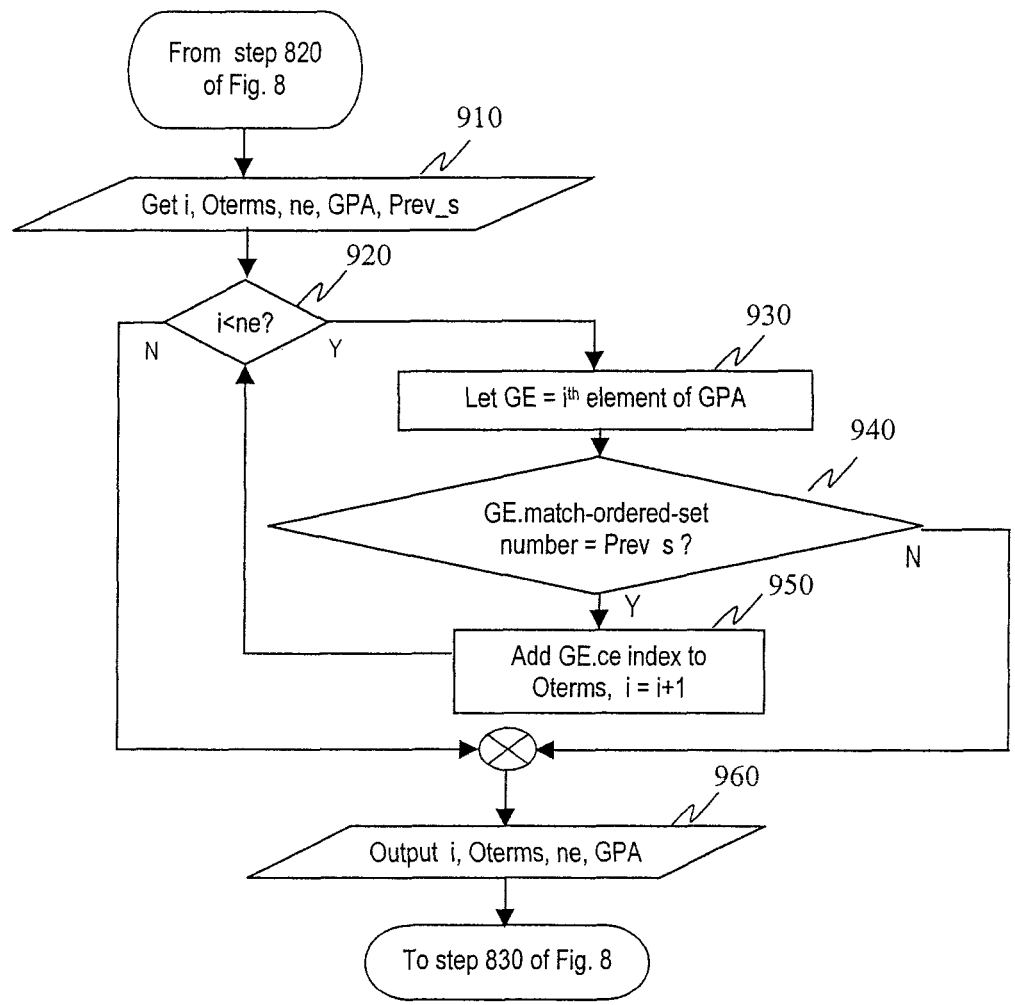
FIG. 9 is a flowchart that provides additional detail of step 825 of FIG. 8 and step 1125 of FIG. 11.

All the complete paths are processed at step 825, additional detail of which is provided in FIG. 9 and the accompanying description.

Step 830 ensures that each element in the FGPA is processed using the loop variable i. If there are still elements of the FGPA to be processed and the set Oterms is not empty (N), at step 830, the set Tterms is re-initialized to empty and the previous layer (Prev_s) is re-initialized to 1 at step 835 (for processing of the next element of the FGPA). Complete paths are built by de-normalizing the path information contained in the rest of the elements of the FGPA at step 840. Additional detail regarding step 840 is provided in FIG. 9. Then, the FGPA is output at step 845. All elements in the FGPA have complete paths from the source node (an element in the layer $V_i$) to the target node (an element in $V_1$) in their array of input nodes.

When the FGPA is processed, all the elements of the FGPA that do not belong to a path from the source layer ($V_i$) to target layer ($V_1$) are removed. Thus all existing/remaining elements will define a path from the source layer to the target layer. The nodes in each layer, including the target and source layer that form the path, are arranged in an array variable containing the input nodes for each remaining element. The first element in the array of input nodes entry is the node in the target layer, the second element is the node in the subsequent layer, and so on. The last entry is the node in the source layer. Hence, this information provides the complete path information.

Alternatively, if all the elements of the FGPA have been processed or the set Oterms is empty (Y), at step 830, the FGPA is output directly at step 845.

FIG. 9 is a flowchart for processing all complete forward paths and corresponds to step 825 of FIG. 8.

Processing variables including the FGPA, the number of elements in the FGPA, the match-ordered set number of the target layer (Prev_s), and the set Oterms are loaded and/or initialized at step 910. Oterms is a global variable that contains information for efficient construction of paths without considering those nodes in the graph that do not terminate at a node in the target layer. Thus, only nodes that belong to a path that terminates at a node in the target layer appear in the Oterms set.

At step 920, it is determined whether all the elements of the FGPA have been processed using the loop variable i. At step 930, a current element of the FGPA is selected.

Then, at step 940, it is determined whether the current element belongs to the target set, which is provided in the variable Prev_s. If so (Y), the element's index in its match-ordered set, which would be used by an entry in the following layer to point to as next node, is added to the Oterms set at step 950. Thereafter, the loop variable i is incremented and processing continues at step 920. All entries belonging to the target set have complete path information in their array of input nodes.

If the current element does not belong to the target set (N), at step 940, or all of the elements of the GPA have been processed (N), at step 920, the processed GPA and associated variables are output or made available to a further processing step at step 960.

Figure 10:
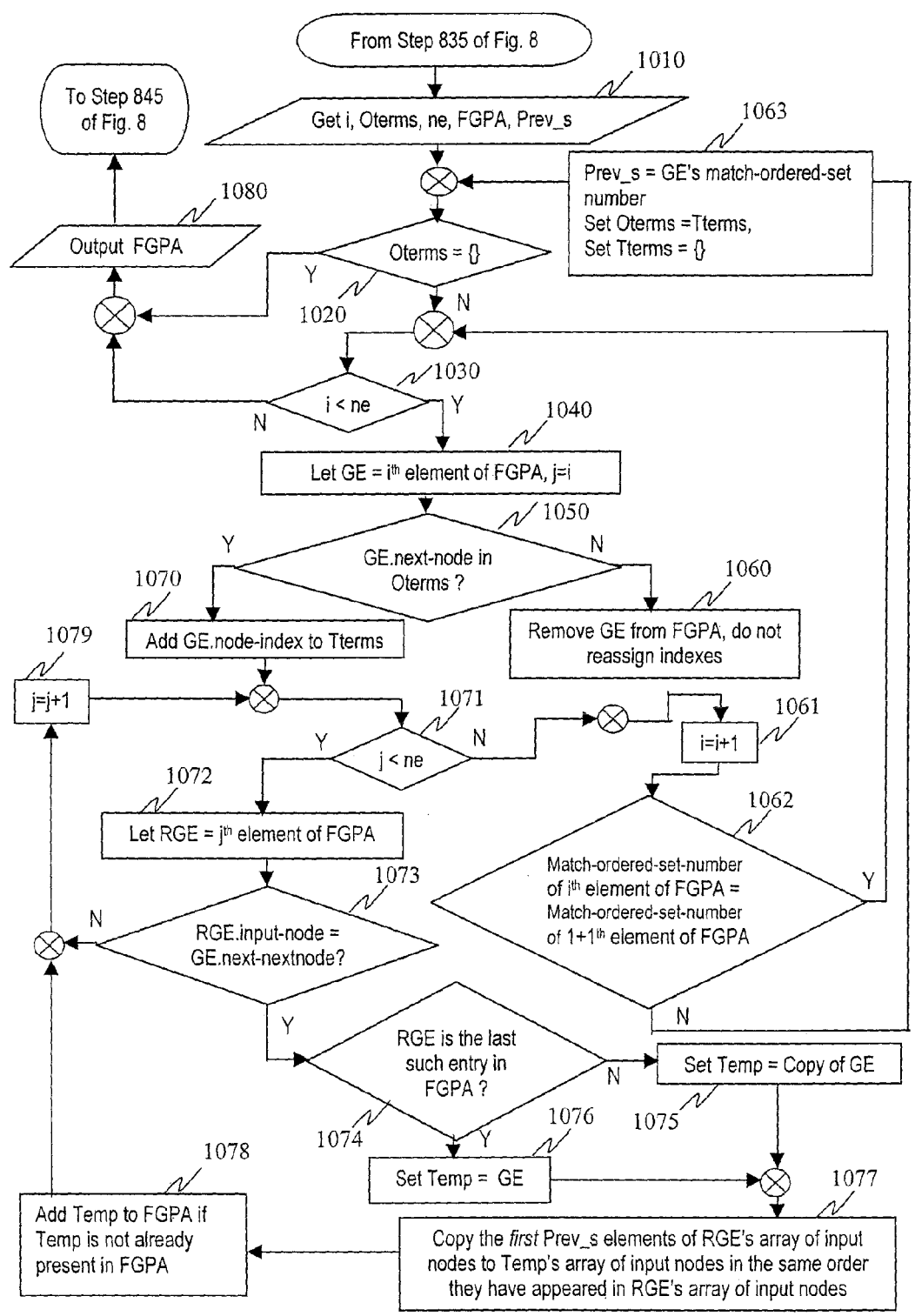
FIG. 10 is a flowchart that provides additional detail of step 840 of FIG. 8.

FIG. 10 is a flowchart of a process for de-normalizing the Forward Global Path Array and corresponds to step 840 of FIG. 8.

Referring to FIG. 10, the FGPA, the number of elements in the FGPA, the starting position for processing in the Forward Global Path Array (FGPA), the number of the layer previously processed (Prev_s) and the nodes in the current layer which form part of a complete path, are loaded at step 1010. The nodes forming part of a complete path are obtained from the sinklayer Oterms. If no complete paths to the previous layer exist, then no paths from the sinklayer to the previous layer via the current layer can exist In this case, the FGPA would not contain any entries for Prev_s and Oterms would be empty.

If Oterms is empty, no paths pass through or terminate at the Prev_s layer since any threads terminating at the Prev_s+1 layer would use the Prev_s layer's nodes, which have paths to the target layer to reach the target node. Thus, if no such nodeS exist in the Prev_s layer, no paths exist from the Prev_s+1 and subsequent layers to the target layer. Accordingly, it is determined at step 1020 whether Oterms is empty. If so (Y), the FGPA is output at step 1080 and processing continues at step 845 of FIG. 8. Alternatively (N), it is determined at step 1030 whether all the elements of the FGPA have been processed, using the loop variable i. If so (N), the FGPA is output at step 1080 and processing continues at step 845 of FIG. 8.

If there are further elements of the FPGA to be processed (Y), at step 1030, internal variables are initialized at step 1040. Then, at step 1050, it is determined whether the next node of the current element of the FGPA being processed is present in Oterms. If so (Y), it is implied that a path exists between the current element of the FGPA and the previous layer (Prev_s), via the next node, and the current element's input node is noted (i.e., the node's index is added to Tterms) at step 1070. This enables nodes in the Prev_s+1 layer that have the current element as their next node, to be processed.

Each element of the FGPA with next node as input node contains path information relating to the path from the element to the target set in the array of input nodes. That information, together with information contained in the current element's array of input nodes, is used to find a path from the sinklayer to the target layer that passes through the current element's input node and next node. The nodes that have to be visited on a path from the current element to an element in the target layer are given by Prev_s, thus, the first Prev_s elements of the matching element are prefixed to the current element's input array of nodes. Hence, complete path information is obtained.

Steps 1071 to 1079 search the entire FGPA for all elements whose next node is an input node. Step 1073 checks for elements whose input nodes match the current element's next node. Step 1077 finds the Prev_s elements from the matched element's array of input nodes and adds those elements to the current element's array of input nodes. Since more than one path via a node can exist, steps 1074, 1075 and 1076 create elements for each path so that no information is lost. Step 1076 reuses the current element if only one path exists or if the current element corresponds to the last path through the node.

When all the elements in the FGPA have been searched relative to a current element (N), at step 1071, a new current element is selected. Step 1060 removes the superceded current element from the GPA to prevent that element being considered during further processing. Step 1061 updates the loop variable i to keep track of the elements still to be searched.

Returning to step 1050, if the next node of the current element is not contained in Oterms (N), it implies that no path exists from the current element to the target node. Accordingly, the next node is selected at step 1061.

At step 1062, it is determined whether the next element belongs to the same match-ordered set. If so (Y), processing returns to step 1030. Alternatively (N), Oterms is updated to include those elements in the current match-ordered set that form part of a path, at step 1063. Prev_s is also updated to the current element's match-ordered set number, at step 1063, so that the number of elements taken to complete the path is correct. The next entry will belong to the Prev_s or Prev_s+1 match-ordered set since the FGPA is sorted in ascending order of the match-ordered set number of the elements.

When either Oterms becomes empty (Y, at step 1020) or all the elements in the FGPA have been processed (N, at step 1030), the processed FGPA is output at step 1080. Each element in the FGPA with length of array of input nodes equal to the distance between the sink layer and the target layer indicates a complete forward path (e.g. if there are 3 intermediate layers between the sinklayer and the target layer, an entry containing 5 elements in the array of input nodes comprises information relating to a complete path).

A pseudo-code algorithm for de-normalizing the Forward Global Path Array is provided hereinafter in Table 5.

TABLE 5

Figure 11:
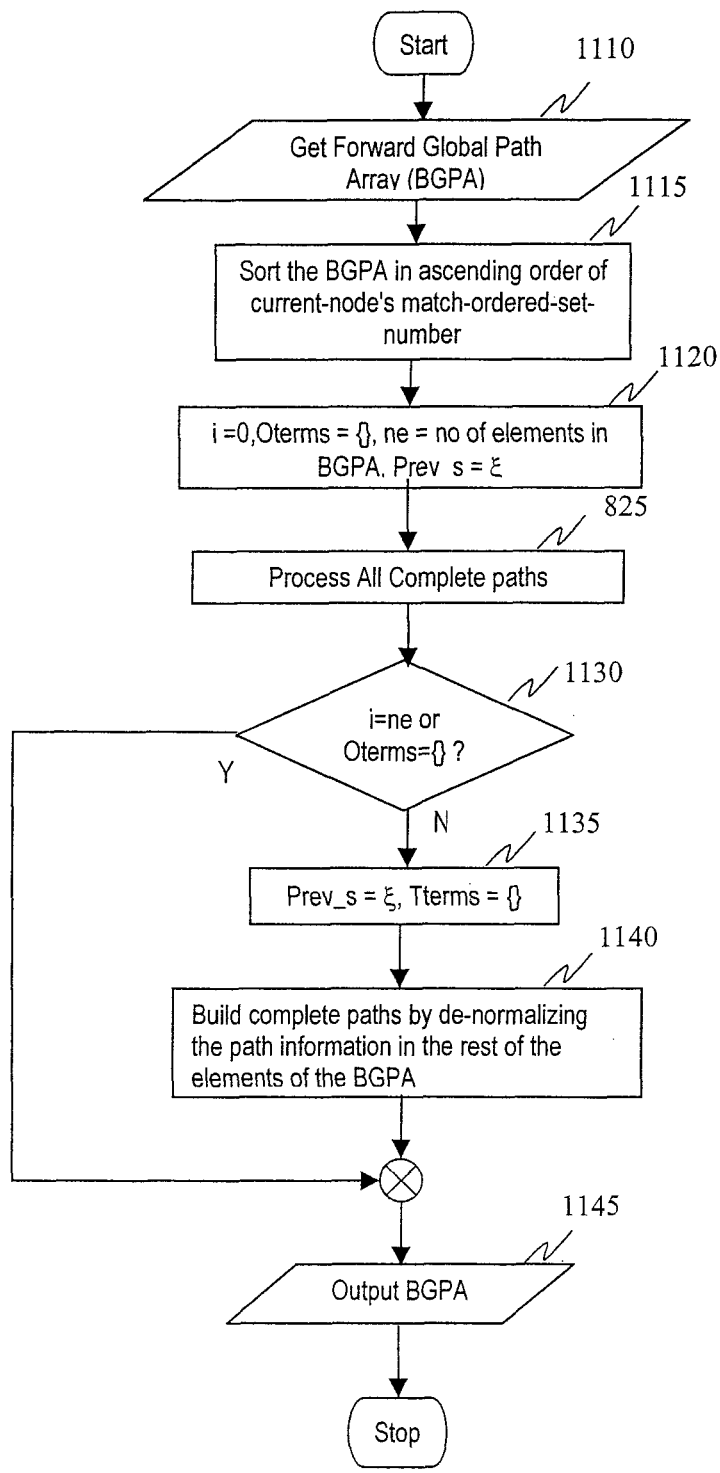
FIG. 11 is a flowchart for building complete paths from the Backward Global Path Array (BGPA)
Figure 12:
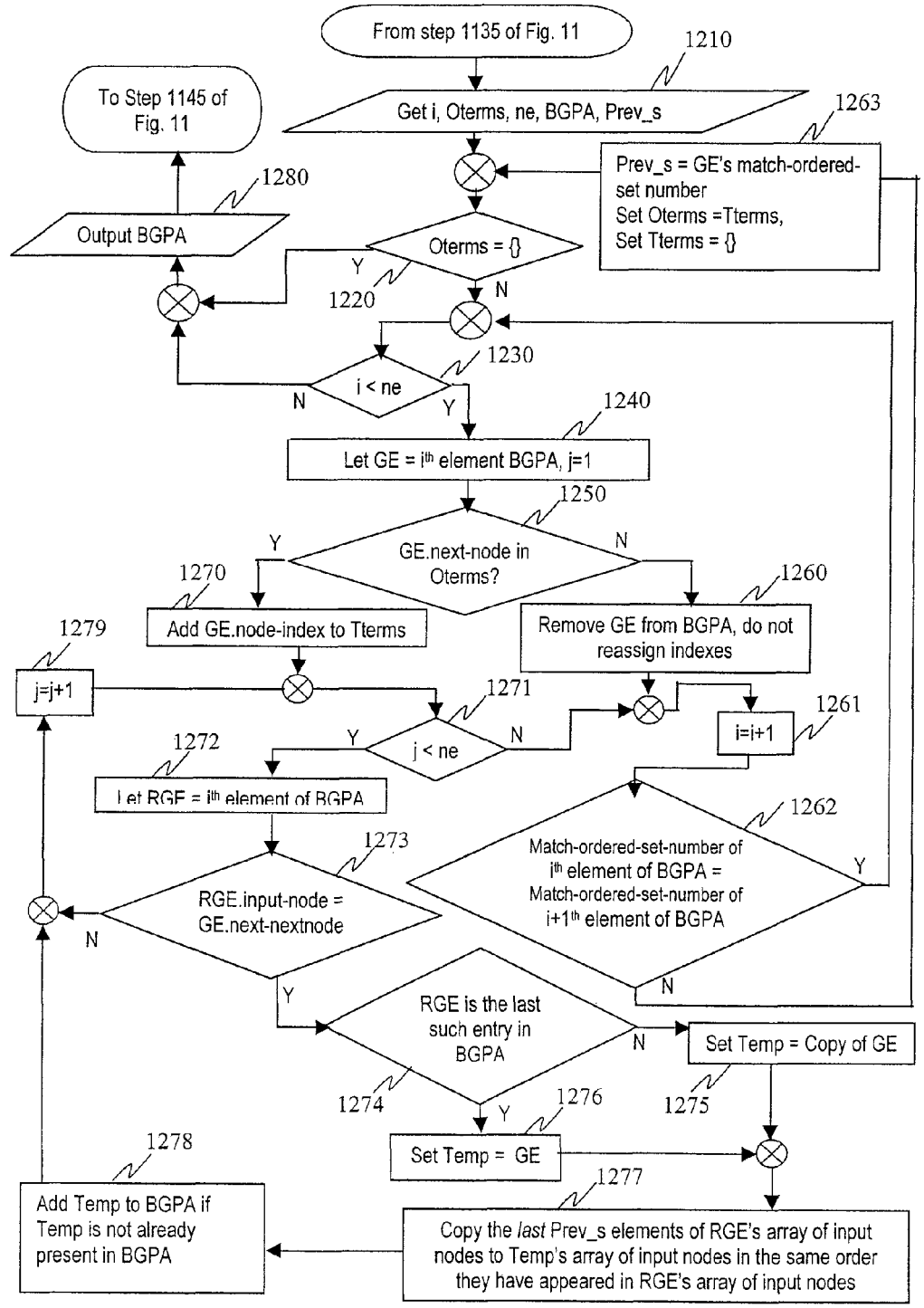
FIG. 12 is a flowchart that provides additional detail of step 1140 of FIG. 11.

Sort the Forward Global Path Array in ascending order of matchOrderedSetNumber
FGPA_L = number of elements in Forward Global Path Array
For each entry in Forward Global Path Array with matchOrderedSetNumber equal to
source node ($V_1$) matchOrderedSetNumber
    Add entry.nodeIndex to Oterms
End-for
If Oterms is a Null-Set then Exit /* No path exist from target (Sink Layer) to the source */
/* The iterator will point to the '$n^{th}$' element in the Forward Global Path Array */
/* For the remaining (FGPA_L − n) entries in the Forward Global Path Array*/
Prev_s = matchOrderedSetNumber of the $(n+1)^{th}$ entry in the Global Path Array
Tterms = { }
For the remaining (FGPA_L−n) entry (cur_e) in the Forward Global Path Array
    If the cur_e.nextNodeIndex is IN Oterms then
        For each entry e1 in the Forward Global Path Array with cur_e.nextNodeIndex =
        e1.nodeIndex
            /* insert in the beginning of cur_e.arrayOfInputNodes, with the first Prev_s
            elements from the e1.arrayOfInputNodes */
            numNodeElem = number of elements in e1.arrayOfInputNodes
            If e1 is the last such entry in Forward Global Path Array then
                Temp = cur_e
            else
                Temp = copy of cur_e
            End-if
            Temp.nextNode index = −1
            For k = Prev_s − 1 to 0
                insert e1.arrayOfInputNodes [k] to the beginning of
                Temp.arrayOfInputNodes
            End for
            Add Temp to end of Forward Global Path Array
        End-for
        Add cur_e.current-node index to Tterms
    Else/* if cur_e.next-node index does not exist in Oterms*/
        Remove cur_e entry from the Forward Global Path Array
    End-if
    If Prev_s != cur_e's next entries.matchOrderedSetNumber then
        Prev_s = cur_e.matchOrderedSetNumber
        Oterms=Tterms
        If Oterms = { } then Exit
    End-if
End-for FIG. 11 is a flowchart of a process to build complete paths in the backward direction, which provides further detail of step 520 of FIG. 5. The output of this process is used by step 535 of FIG. 5. An appropriately skilled addressee will readily recognize that the method in the backward direction is similar to that in the forward direction (i.e., FIG. 8). Additional detail of step 1125 of FIG. 11 is provided in FIG. 9, which applies to both the forward and backward directions. Additional detail of step 1140 of FIG. 11 is provided in FIG. 12, which is a flowchart of a process for de-normalizing the Backward Global Path Array. Once again, the method for de-normalization in the backward direction is similar to that for the forward direction and the skilled addressee is referred to the description relating to FIG. 10. The differences between the forward and backward directions primarily relate to the GPA and Prev_s, as follows:

The Backward Global Path Array (BGPA) is sorted in descending order of the match-ordered set number of the entries Prev_s is decremented by 1 each time since the next entry's match-order set number can only decrease The last Prev_s entries of the arrayOfInputNodes of the entry whose input node matches the current entry's next node is added to the end of the current entry's arrayOfInputNodes.

Finally, the Forward and Backward Global Path Arrays are merged to find the optimal sequence set, according to the following:

Select all paths that satisfy the sequence length constraint,

Calculate $\Sigma vs_{i_{max}}$ ($0 \leq i < m$), where the desired weight $vs_{i_{max}}$ corresponds to the highest scoring element $vs_{max}$ of set $V_i$, Calculate the path weight $\Sigma weight(e)$ for all the selected paths, and Drop all the paths whose path weight is less than (the desired weight*(1−T)) or greater than (the desired-weight*(1+T)).

Each of the paths are represented by (x, y) pairs where x=v.start from $V_1$ and y=v.start from $V_\zeta$ represent the starting and ending points, respectively, of an instance of sequence G in string S. All the remaining selected paths form the set <G>.

Matching with Mismatches and Synonyms

A simple string-matching algorithm will generally produce the best results. However, in the context of the current problem, the following requirements must be met:

Since the data being dealt with is inherently noisy and has multiple representations (for example, when synonyms occur), use of an exact string-matching algorithm will frequently result in the method terminating in the first step. Accordingly, the matching method should allow for an amount of mismatches and/or identify synonyms as matches and/or allow insertions and deletions of some parts in the target sequence (which might arise due to errors in transmission media, etc.), while identifying similarity.

The method should not, however, be too insensitive in which case a large number of matches (some of which may be negative samples) may occur, resulting in decreased performance and also decreased significance.

As a result of the foregoing requirements, a matching technique that produces positive samples, whilst being lenient enough to allow for insertion and deletion errors and capable of handling synonyms, is used. Positive samples comprise samples in a search space of a matching process that can be considered to represent matches. The sensitivity of the matching technique can be fine-tuned to the specific requirement of a particular target application. A matching technique, based on a mismatch score, is described hereinafter (appropriate modifications have to be made to base the technique on a match score):

A marker string $m_i \epsilon M$ is said to match a substring SS of string S if, and only if, the mismatch score of the marker string $m_i$ against SS is less than $s_i$. The mismatch score is calculated as follows:

A current symbol $SS_j$ of the substring SS is input to a set of automata that exist at the beginning of the current matching process and a new automata is created with $SS_j$ as the start symbol. The marker string $m_i$ is also passed to enable identification of the synonyms of $m_i$.

If any one of the automata recognize a word, the automata fires signifying a match.

The weight of the word recognized is subtracted from the mismatch score. The weight of the word (synonym) is the mismatch score of the word against the sub-profile $p_{ijk}$, where j is the position where the automaton was created and k is the position where the automaton fired.

The process is repeated with the next symbol $SS_{j+1}$.

If none of the automata fire the process continues as follows:

If $m_{ij}$ does not match $SS_j$, and there is no row corresponding to symbol $m_{ij}$ in the profile, then add 1 to mismatch. Otherwise, if a non-zero value (v) is found against the symbol $m_{ij}$ in the profile at column j of $p_i$, then (1−v) is added to the mismatch count. This score is calculated for the entire length of the $m_i$ (ie. the sum of $m_{ij}$ for $0 < j < l_i$) is called the mismatch score (z). Actually, the match score is $(l_i-z)$ but, since this score is used to rank the various matches of $m_i$ against S, the use of min z instead of max $(l_i-z)$ doesn't make a difference. When the matching process for $m_i$ and SS is completed, the automata's are not destroyed if the next sub-string SS contains all except $SS_0$ of the current sub-string SS. However, if any of the automata fire, then the match/mismatch score is set to zero. This allows for variations in length so that mismatches due to insertions or deletions of some character in the beginning of the sequence is mitigated. Edge effects are also taken care of.

Figure 13:
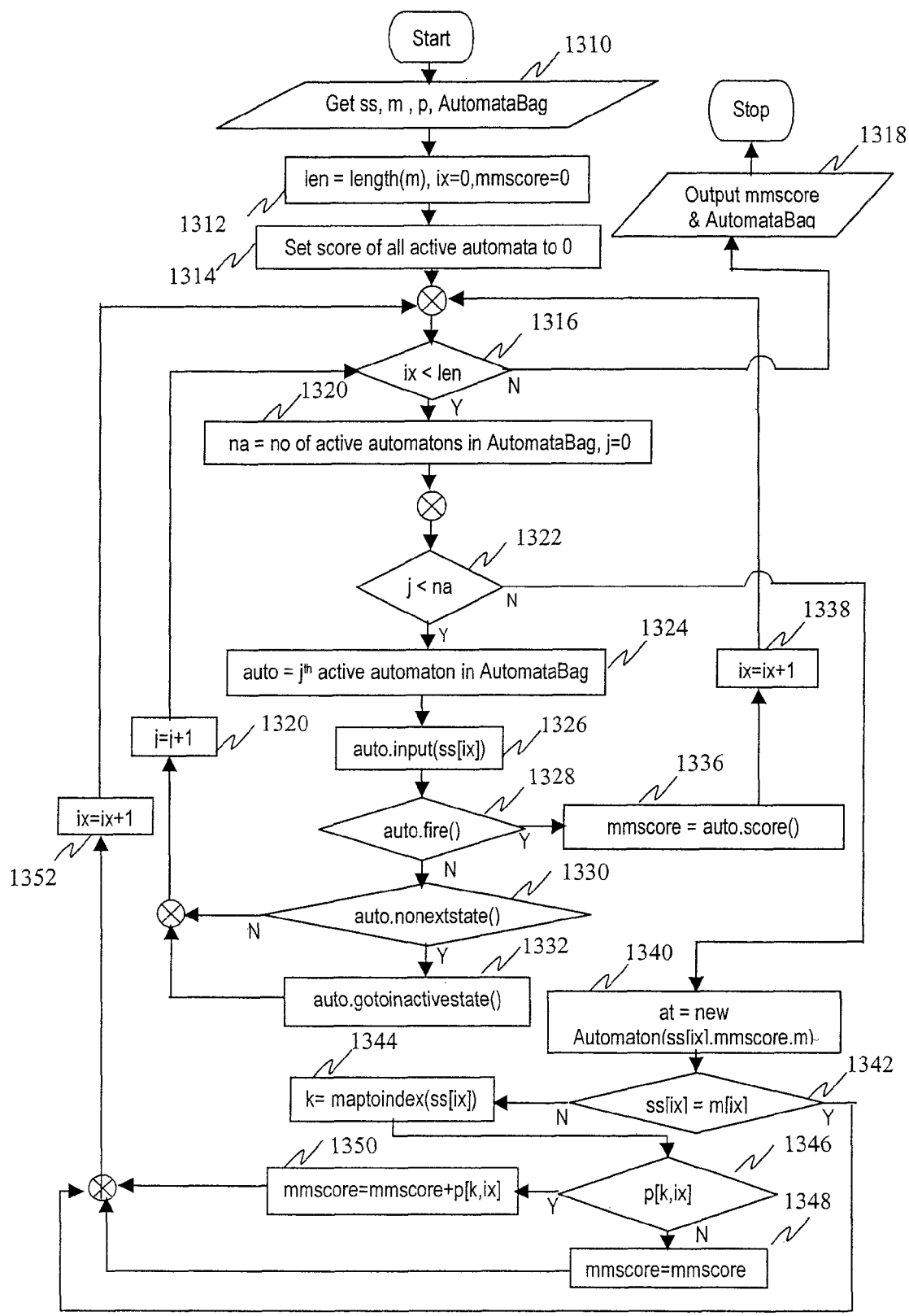
FIG. 13 is a flowchart of a method for a matching process according to an embodiment of the present invention.

FIG. 13 is a flowchart of the matching technique described hereinbefore. A pseudo-code algorithm for the matching technique is also presented in Table 6 hereinafter.

Referring to FIG. 13, the sub-string to be matched ss, the marker string m against which ss is to be matched, the profile p to be used in the matching process and an automatabag are loaded at step 1310. An automatabag is a data structure that manages automatons and provides facilities to create, locate and remove automata. When the matching process for ss starts afresh or all the automata created up until the previous step become inactive, the automatabag may be empty.

Various internal variables used in the matching process are initialized at step 1312. At step 1314, all the active automata scores are reset to zero so that if any automata subsequently fire, the mismatch score is made zero. If an automaton's score is not set to zero, upon identification of a synonym, etc., the current mismatch score will be set to the mismatch score carried when the automaton was created. Some of the automatons are created during a previous matching step, thus, automatons that stay alive are typically created near the end of the previous matching process and may carry a high penalty score. The current mismatch score should not be biased as a result thereof.

The process of FIG. 13 utilizes a mismatch score, hence the mismatch score is made zero whenever an automaton that existed at the beginning of the matching process fires. However, were the process to be adapted to use a match score, the variable used for scoring the match score should be set to zero and the score for recognizing the codon/word that the automata recognized should be added to the match score variable.

Step 1316 determines whether all the characters in the sub-string ss have been processed using the loop variable ix. If not (Y), steps 1320 and 1324 provide input to each automata in the automatabag. At step 1326, the current character is input to an active automaton selected at step 1322 using loop variable j.

At step 1328, it is determined whether the selected automaton has fired (i.e., a synonym or word in the language has been identified). If so (Y), the score is adjusted at step 1336 to eliminate the penalty whenever an automaton fires, the loop variable ix is incremented at step 1338 for selecting the next character in the sub-string ss and processing continues at step 1316. If the selected automaton has not fired (N), steps 1330 and 1332 remove automatons relating to words that cannot be identified by making those automatons inactive. Thereafter, loop variable j is incremented at step 1334 for selection of the next active automaton and processing continues at step 1316.

When there are no more automatons (N), at step 1322, a new automaton is created with the current character and score at step 1340 such that, if a synonym or word starting with the current character exists in the sub-string ss, the automaton will fire and the score of the sub-string ss will be adjusted. In essence, the sub-string's score reverts back to the score stored in the automaton upon creation thereof as the penalties added to the score up until the point where the automata fires have to be removed when a sub-word is found as a synonym.

At step 1342, it is determined whether the current character from the marker string and the current character from the sub-string match. If so (Y), the loop variable ix is incremented for selection of the next character of the sub-string ss at step 1352 and processing continues at step 1316. If the current character from the marker string and the current character from the sub-string do not match (N), it is determined, at steps 1344 and 1346 whether the profile contains a penalty associated with the current character of the substring ss at the particular position. The profile may not contain a penalty for the current character of the substring ss occurring at a particular position if such a condition did not occur in the samples used to build the profile.

If a corresponding penalty is contained in the profile (Y), at step 1346, the penalty is added to the score at step 1350. Thereafter, the loop variable ix is incremented for selection of the next character of the sub-string ss at step 1352 and processing continues at step 1316. All penalties contained in the profile are fractional (i.e., less than 1).

Alternatively, if a corresponding penalty is not contained in the profile (N), at step 1346, the maximum per-character penalty of 1 is added to the score at step 1348. Thereafter, the loop variable ix is incremented for selection of the next character of the sub-string ss at step 1352 and processing continues at step 1316.

Once the score has been calculated for a sub-string ss (N), at step 1316, the automatabag and the score are output at step 1318. The automatabag is reused for matching of the subsequent sub-string ss1 to enable synonyms across window boundaries to also be identified. As large sequences are cut into smaller sub-strings and processed, the length of the substring plays an important role. However, the substring ss will typically vary very little to the subsequent sub-string ss1. For example:
s=acgtata
ss=acgta
ss1=cagta

TABLE 6

Input: $ss_i, m_i, p_i$ // $ss_i$ target string, $m_i$ required string, $p_i$, profile
Output: mismatchscore
For ix=0 to length($m_i$)
    automatonfired=false
    For each automaton autom in active state and automatonfired = false
        autom.nextToken($ss_i$(ix)) // $ss_i$(ix) return the $ix^{th}$ alphabet in $ss_i$
        If autom.fire( ) = true then
            mismatchscore = autom.score( )
            automatonfired=true
        else If autom.noNextState( ) then
            autom.gotoInActiveState( )
        End If
    End for
    If automatonfired = false then
        Create new automaton autom($ss_i$(ix),mismatchscore,mi)
        autom.getActive( )
        If $ss_i$(ix)≠$m_i$(ix) then
            Elementfound=false
            For each row r in $p_i$
                If rowelement(r) = $ss_i$(ix) then
                    mismatchscore= mismatchscore+(1−$p_i$(r,ix))
                    elementfound=true
                End if
            End For
            If elementfound=false then
                mismatchscore= mismatchscore+1
            End If
        End If
    End If
End For
Return mismatchscore An automation is an abstract machine that recognises words in the language formed by {Σ,Gr} and is necessary for recognition and matching of synonyms. The automaton collapses on recognition of a word in the language or when there is no next state for the current input symbol. If a next state for the current input exists, the automaton goes to that state. Recognition of a word by the automaton is indicated through an interface (this is known as 'firing') to the matching process.

If a language formed by Σ has no punctuation symbols, many reading frames will exist. This is taken care of by the creation of an automaton for each symbol at each position of the target string with that symbol as the starting state for the automaton. Alternatively, if the language has punctuation symbols, the punctuation information must be used in the automaton design process to enable correct recognition of the words by the automaton. For example, in English, the words 'the' and 'there' both have the same root 'the'. The automaton therefore has to look ahead to recognize words correctly and should not trigger when the root is found. If there are no synonyms in the language, use of the automata are unnecessary.

The profile used in matching also plays an important role in the algorithm's sensitivity for identifying matching pairs. Numerous methods and techniques exist for generating such profiles—the choice of method depends on the target application. A technique that is relatively application independent, is simple to construct and has high sensitivity to positive samples, is described hereinafter.

As described hereinbefore, a profile p is a l×k matrix, wherein p corresponds to m∈M, k is the length of m and l is the number of elements in Σ' (the alphabet of m). The cell values of the profile are obtained experimentally (i.e., by sampling a sufficient number of target strings to which the profile has to match).

Example

Let the target strings be:
'abcde'
'accde'
'abcce'
'a_cde'
Thus, the alphabet Σ'{a,b,c,d,e,_}. The profile for the foregoing 4 target strings is shown in Table 7 hereinafter.

TABLE 7

| Position/Element | 1 | 2 | 3 | 4 | 5 |
|---|---|---|---|---|---|
| A | 1 | 0 | 0 | 0 | 0 |
| B | 0 | ½ | 0 | 0 | 0 |
| C | 0 | ¼ | 1 | ¼ | 0 |
| D | 0 | 0 | 0 | ¾ | 0 |
| E | 0 | 0 | 0 | ½ | 1 |
| _ | 0 | ¼ | 0 | 0 | 0 |

The cell values are calculated using the following formula:

$$C_{ij} = \Sigma e_k/n$$

where:
$e_k \in \Sigma'$, and
n is the number of sample target strings.
$C_{ij}$ represents the frequency of the symbol $e_k \in \Sigma'$ at a position j in the set of representative samples. For example, if $e_k$='B' and position j=2, the number of times 'B' occurs in the second position of the four strings is once. This number is then divided by the number of sample target strings and results in a value of ¼.

For some applications the symbol '_' may represent any of the alphabets in Σ-'_'. In this case, each cell in the column in which the symbol occurs can be incremented by 1/(n−1) for each occurrence of the symbol, excluding the cell that corresponds to that symbol in the column.

The cell values are normalized as follows:
For each column in the generated profile, locate the non-zero positive solution for $\Sigma C_i \exp(\lambda C_i)=1$ and multiply each cell in the column by λ.
If no non-zero solution exits then the cell values are not disturbed (such a condition arises only when data has been overfitted and this condition has to be taken into consideration when the cut-off score is being determined).
The final matrix is the required profile.

Use of the above profile construction technique reduces the relative entropy since the profile is constructed from a known distribution and the target match is also required to belong to a similar distribution. Thus, if matching is performed against a random sequence then the condition $\Sigma p_i ss_i < 0$ is met. This allows the matching to be more insensitive to random strings and hence the chance of random strings being identified is greatly reduced.

The reason why relative entropy is reduced is as follows:
Given a scoring matrix and a model sequence generated independently identically distributed according to some background distribution P, the maximal scoring segment (MSS) within the sequence can be identified. The complete, full-length sequence represents one message, while the MSS reported by an embodiment of the present invention constitutes another. For example, a hydrophobicity scoring matrix that assigns increasingly positive scores to more hydrophobic amino acids, zero score to amphipathic residues, and increasingly negative scores to more hydrophilic residues, can be created. By searching for the MSS—the "most hydrophobic" segment in this case—a portion of the sequence whose letters exhibit a different, hydrophobic distribution than the random background is selected. By convention, the distribution of letters in the MSS is called the target distribution Q. If the letters in the MSS are described using an optimal Shannon code for the background distribution, a longer description is expected than for a code optimized for the target distribution. The extra bits—the extra description length—indicate the relative odds that the MSS arose by chance from the background distribution rather than the target. Similarly, in the current context, a gene can be found in many genomes whose background frequencies vary considerably. However, the target distribution is of interest on account of remaining similar or identical for a given gene/marker. When building the substitution matrices, the background frequencies are assumed to be independently identically distributed.

The existing substitution matrices can be used, however the target sequence should be identically distributed to those sequences that were used to build the substitution matrix. DNA substitution matrices will not be sensitive enough if the target sequence and marker's background distribution vary considerably. When the marker is constructed by observing the gene's signature in various organisms, which is often the case, the rate of mutations (of bases) among these organisms will vary and cannot be satisfactorily combined to reflect the genomes collectively. If the target genome's position in the generation tree does not fall within the first few generations, a great deal of variation in the observed mutation and the expected mutation will also result (the mutation rate based on which the marker was constructed). Thus, in situations where the profile has to constructed from sources that need not be closely related (such as the E. coli and human genome), the above-mentioned technique works best.

If the profiles are constructed using the above-mentioned method then the cut-off score used to identify matching and non-matching segments plays a very important role. The value of the cut-off score has to be identified using statistical techniques. For example, generate random sequences from distributions which closely model genomic data, use actual sequences that have to be identified and mutated sequences (allowable mutations). Find the scores that get generated when the profile is used to match against each of these sequences, based on the misclassification cost that you are allowed to use select the score that divided this space into regions that are considered mismatches and matches. Hence the above method is generic and applicable to all circumstances.

The use of profiles is simpler than other methods and the effectiveness of the profiles can be statistically determined. The construction of profiles does not require negative samples nor the training process associated with neural networks. Use of automata in conjunction with profiles results in a relatively more flexible method that offers all the features of a neural network solution at no additional cost.

Normalization of Scoring and/or Searching Spaces

The score for a path is the sum of the scores of each $v_i$ occurring in the path. However, scores that are not normalized to their length and weight cannot be added due to a difference in search space and scoring space.

An example of an unnormalized search space is that long strings possess high scores even when not very good matches. Short strings possessing a relatively higher degree of similarity may, however, score lower than longer strings on account of their relative length.

An example of an unnormalized scoring space is when strings evaluated by a first scoring system are compared to strings evaluated by another scoring system that uses much greater weights than the first scoring system.

Hence, it is necessary and/or advantageous that scores be normalized before addition and comparison. Moreover, each $vs_{max}$ should be normalized before calculating the desired weight. Thus, the arc weight of an arc e is given by:

$$weight(e) = N(v_i, length(v_i)) + N(v_j, length(v_j))$$

where:
 $N(x, l)$ is a normalizing function.

A Normalizing Function

For two sequences $A = \{x_1, x_2, \ldots x_n\}$ and $B = \{y_1, y_2, \ldots y_n\}$, the matching score not allowing for gaps is defined as:

$$H_i = \Sigma Sf(x_i, y_i)$$

where:
 $Sf(x,y)$ denotes the score for matching alphabet x with alphabet y $(x, y \in \Sigma)$.

If A and B are independently, identically distributed, then $Sf(x,y)$ is designed such that the expected score per alphabet is negative. This condition holds for the PAM and BLOSUM scoring families used in protein alignments, and described in the paper entitled "*Methods for assessing the statistical significance of molecular sequence features by using general scoring schemes*", by Karlin, S. and Atschul, S. F., as described hereinbefore.

It has been proved that:

$$\lim_{n \to \infty} H_n / \log(n^2) = \theta$$

holds with probability 1. The limit $\theta$ can be calculated analytically—for further details, the reader is referred to two papers by Dembo, A. and Karlin, S.:

"*Strong limit theorems of empirical functionals for large exceedances of partial sums of i.i.d. variables*", Ann. Prob., 19, 1737-1755; and "*Strong limit theorems of empirical functionals for large exceedances of partial sums of Markov variables*", Ann. Prob., 19, 1756-1767;

both of which are referenced in the paper entitled "*Statistics of large-scale sequence searching*" by Sprang, R. and Vingron, M., as described hereinbefore.

The length adjusted score for a match is given by:

$$A_s = H - \log(n)\theta$$

where:
 H is the score obtained from the matching function, and
 n is the length of the strings being matched.

The function $N(x, l)$ can now be defined as follows:

$$N(x, l) = x - \log(l)\theta \quad (1)$$

Equation (1) caters for search space differences, but not for scoring space differences, when normalizing scores. If a uniform scoring space is used for all the matches (i.e., the profiles for all $m_i \in M$ belong to the same scoring space), then equation (1) would suffice. If, however, the profiles vary in scoring space, then the scores need to additionally be normalized against the scoring space. A scoring space is characterized by its natural scoring scale (λ). The value for λ can be calculated analytically for the scoring system and is a unique positive solution of the equation:

$$\sum p_i \exp(\lambda s_i) = 1$$

where:
$1 \leq i \leq r$
r is the cardinality of $\Sigma'$ of $m_i$,
$p_i$ represents the probability of occurrence of alphabet i in $\Sigma'$,
$s_i$ is the score associated with that alphabet in the scoring system.

The function N(x,l) can now be defined as follows:

$$N(x,l) = \lambda(x - \log(l)\theta) \quad (2)$$

The result of N(x,l) is in natural scale. This can be changed to any target scale by dividing equation (2) by the natural logarithm of the base of the target system.

The following equation gives the score in terms of Bit score:

$$N_b(x,l) = \lambda(x - \log(l)\theta)/\ln 2 \quad (3)$$

Computational Requirements

The time complexity of the algorithm described herein increases as a function of the number of marker strings $m_j$. However, the algorithm has been described as a sequence of steps that are inherently parallel in nature:

STEP A: Matching set $V_i$ for each marker string $m_i$ can be found independently of the other marker strings $(M - m_{i+})$.

STEP B: The graph $\Omega$ can be built by comparing adjacent V sets $(V_i, V_{i+1})$ to obtain edges independently of the other V sets.

STEP C: Each path in the graph that connects an element in $V_1$ to $V_\zeta$ can be found in parallel.

Parallelism constitutes a major advantage of the algorithm described herein. If there are n nodes and m strings in M, and k represents the average time taken to perform a match, then the matching step can be completed in O(mk/n) time. The arc generation step can be completed in O(m/2n) time.

Computer Hardware and Software

Figure 14:
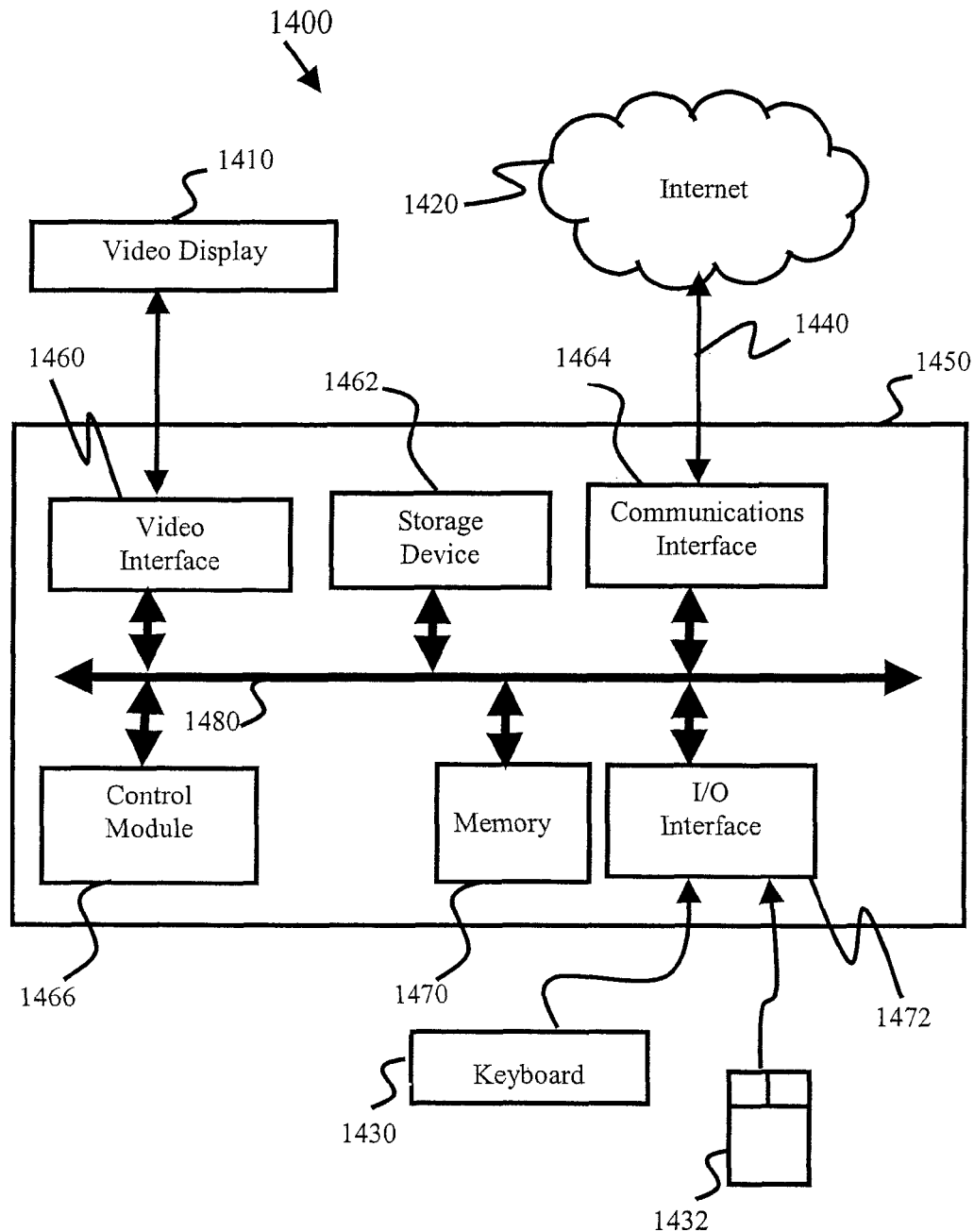
FIG. 14 is a block diagram of a computer system suitable for performing the methods and/or techniques of embodiments of the present invention, as described hereinafter.

The methods, processes and/or algorithms described hereinbefore can be implemented using a computer program product in conjunction with a computer system 1400 as shown in FIG. 14. In particular, the methods, processes and/or algorithms described hereinbefore can be implemented as software, or computer readable program code, executing on the computer system 1400.

The computer system 1400 includes a computer 1450, a video display 1410, and input devices 1430, 1432. In addition, the computer system 1400 can have any of a number of other output devices including line printers, laser printers, plotters, and other reproduction devices connected to the computer 1450. The computer system 1400 can be connected to one or more other computers via a communication interface 1464 using an appropriate communication channel 1440 such as a modem communications path, an electronic network, or the like. The network may include a local area network (LAN), a wide area network (WAN), an Intranet, and/or the Internet 1420.

The computer 1450 includes the control module 1466, a memory 1470 that may include random access memory (RAM) and read-only memory (ROM), input/output (I/O) interfaces 1464, 1472, a video interface 1460, and one or more storage devices generally represented by the storage device 1462. The control module 1466 is implemented using a central processing unit (CPU) that executes or runs a computer readable program code that performs a particular function or related set of functions.

The video interface 1460 is connected to the video display 1410 and provides video signals from the computer 1450 for display on the video display 1410. User input to operate the computer 1450 can be provided by one or more of the input devices 1430, 1432 via the I/O interface 1472. For example, a user of the computer 1450 can use a keyboard as I/O interface 1430 and/or a pointing device such as a mouse as I/O interface 1432. The keyboard and the mouse provide input to the computer 1450. The storage device 1462 can consist of one or more of the following: a floppy disk, a hard disk drive, a magneto-optical disk drive, CD-ROM, magnetic tape or any other of a number of non-volatile storage devices well known to those skilled in the art. Each of the elements in the computer system 1450 is typically connected to other devices via a bus 1480 that in turn can consist of data, address, and control buses.

The methods, processes and/or algorithms described hereinbefore are effected by instructions in the software that are carried out by the computer system 1400. Again, the software may be implemented as one or more modules for implementing the method steps.

In particular, the software may be stored in a computer readable medium, including the storage device 1462 or that is downloaded from a remote location via the interface 1464 and communications channel 1440 from the Internet 1420 or another network location or site. The computer system 1400 includes the computer readable medium having such software or program code recorded such that instructions of the software or the program code can be carried out.

The computer system 1400 is provided for illustrative purposes and other configurations can be employed without departing from the scope and spirit of the invention. The foregoing is merely an example of the types of computers or computer systems with which the embodiments of the invention may be practiced. Typically, the processes of the embodiments are resident as software or a computer readable program code recorded on a hard disk drive as the computer readable medium, and read and controlled using the control module 1466. Intermediate storage of the program code and any data including entities, tickets, and the like may be accomplished using the memory 1470, possibly in concert with the storage device 1462.

In some instances, the program may be supplied to the user encoded on a CD-ROM or a floppy disk (both generally depicted by the storage device 1462), or alternatively could be read by the user from the network via a modem device connected to the computer 1450. Still further, the computer system 1400 can load the software from other computer readable media. This may include magnetic tape, a ROM or integrated circuit, a magneto-optical disk, a radio or infra-red transmission channel between the computer and another device, a computer readable card such as a PCMCIA card, and the Internet 1420 and Intranets including email transmissions and information recorded on Internet sites and the like. The foregoing are merely examples of relevant computer readable media. Other computer readable media may be practised without departing from the scope and spirit of the invention.

The methods, processes and/or algorithms described hereinbefore can be realised in a centralised fashion in one computer system 1400, or in a distributed fashion where different elements are spread across several interconnected computer systems.

Computer program means or computer program in the present context mean any expression, in any language, code or notation, of a set of instructions intended to cause a system having an information processing capability to perform a particular function either directly or after either or both of the following: a) conversion to another language, code or notation or b) reproduction in a different material form.

The computer system 1400 is described for illustrative purposes: other configurations or types of computer systems can be equally well used to implement the described techniques. The foregoing is only an example of a particular type of computer system suitable for implementing the described techniques.

CONCLUSION

A method, a system and a computer program product have been described for for identifying one or more occurrences of a sequence of ordered marker strings in a string. Various modifications and substitutions can be made to the techniques and arrangements described herein, as would be apparent to one skilled in the relevant art in the light of this disclosure, without departing from the spirit and scope of the invention.

We claim:

1. A method for finding a gene in a DNA sequence (S), said gene represented by an ordered set of M distinct marker strings $m_1, m_2, \ldots, m_m$, said M at least 3, said method comprising the steps of:

for i=1, 2, ..., M, identifying a sub-string $V_i$ in S, wherein sub-string $V_i$ consists of J identical elements $V_{ij}$ (j=1, 2, ..., J) such that $V_{ij}$ specifies a sequential position number $P_j$ in S at which $m_i$ is located in S, wherein each identical element $V_{ij}$ in $V_i$ consists of $m_i$, wherein $V_{ij}$ are ordered in sub-string $V_i$ such that $P_1 < P_2, \ldots < P_J$, wherein J is a function of i, and wherein J is at least 2 for each i;

for each sub-string $V_i$ (i=1, 2, ..., M−1), a processor of a computer system creating a plurality of directed links from specific elements of sub-string $V_i$ to specific elements of sub-string $V_{i+1}$, subject to said directed links satisfying a same inter-marker length constraint for each directed link;

said processor tracing all paths that connect sub-string $V_1$ to sub-string $V_M$ using said directed links, wherein said paths satisfy a sequence length constraint; and storing said traced paths in a storage device of a computer system, wherein said same inter-marker length constraint is selected from the group consisting of a difference between a position number within the set of specific elements of $V_i$ and a position number within the set of specific elements of $V_{i+1}$ for each directed link being a specified constant value, a difference between a position number within the set of specific elements of $V_i$ and a position number within the set of specific elements of $V_{i+1}$ for each directed link being less than a specified constant value, and a difference between a position number within the set of specific elements of $V_i$ and a position number within the set of specific elements of $V_{i+1}$ for each directed link being more than a specified constant value, and wherein each specified constant value differs from zero.

2. The method of claim 1, wherein said step of identifying sub-strings $V_i$ (i=1, 2, ..., M) in S includes the sub-steps of:

generating a score representative of the degree of match between the marker string $m_i$ and the sub-string $V_i$ in said DNA sequence, using a profile corresponding to said marker string; and determining that said score satisfies a predetermined constraint.

3. The method of claim 2, wherein said profile is representative of a grouping of strings selected from the group consisting of a set of strings that match said marker string, a set of strings that do not match said marker string, and a combination thereof.

4. The method of claim 1, wherein said sequence length constraint is selected from the group consisting of a minimum number of characters, a maximum number of characters, and a predetermined number of characters.

5. The method of claim 1, wherein the method further comprises:

recording, in a set ordered according to the occurrence of said marker strings in said ordered set of marker strings, a score of each sub-string such that the score of each sub-string satisfies a matching constraint, and wherein the sum of the scores of the sub-strings is within a predetermined tolerance of a designated path score.

6. The method of claim 1, wherein the method further comprises:

de-normalizing path information of each traced path.

7. The method of claim 6, wherein the path information of each traced path to be de-normalized is stored in a global path array in the normalized form.

8. A computer program product comprising program code recorded on a machine-readable device, said program code upon being executed by a processor of a computer system implements a method for finding a gene in a DNA sequence, said gene represented by an ordered set of distinct marker strings, said method comprising the steps of:

for i=1, 2, ..., M, identifying a sub-string $V_i$ in S, wherein sub-string $V_i$ consists of J elements $V_{ij}$ (j=1, 2, ..., J) such that $V_{ij}$ specifies a sequential position number $P_j$ in S at which $m_i$ is located in S, wherein each identical element $V_{ij}$ in $V_i$ consists of $m_i$, wherein $V_{ij}$ are ordered in sub-string $V_i$ such that $P_1 < P_2, \ldots < P_J$, wherein J is a function of i, and wherein J is at least 2 for each i;

for each sub-string $V_i$ (i=1, 2, ..., M−1), creating a plurality of directed links from specific elements of sub-string $V_i$ to specific elements of sub-string $V_{i+1}$, subject to said directed links satisfying a same inter-marker length constraint for each directed link;

tracing all paths that connect sub-string $V_1$ to sub-string $V_M$ using said directed links, wherein said paths satisfy a sequence length constraint; and storing said traced paths in a storage device of the computer system, wherein said same inter-marker length constraint is selected from the group consisting of a difference between a position number within the set of specific elements of $V_i$ and a position number within the set of specific elements of $V_{i+1}$ for each directed link being a specified constant value, a difference between a position number within the set of specific elements of $V_i$ and a position number within the set of specific elements of $V_{i+1}$ for each directed link being less than a specified constant value, and a difference between a position number within the set of specific elements of $V_i$ and a position number within the set of specific elements of $V_{i+1}$ for each directed link being more than a specified constant value, and wherein each specified constant value differs from zero.

9. The computer program product of claim 8, wherein said step of identifying sub-strings $V_i$ (i=1, 2, ..., M) in S includes the sub-steps of:

generating a score representative of the degree of match between the marker string $m_i$ and the sub-string $V_i$ in said DNA sequence, using a profile corresponding to said marker string; and determining that said score satisfies a predetermined constraint.

10. The computer program product of claim 9, wherein said profile is representative of a grouping of strings selected from the group consisting of a set of strings that match said marker string, a set of strings that do not match said marker string, and a combination thereof.

11. The computer program product of claim 8, wherein said sequence length constraint is selected from the group consisting of a minimum number of characters, a maximum number of characters, and a predetermined number of characters.

12. The computer program product of claim 8, wherein the method further comprises:

recording, in a set ordered according to the occurrence of said marker strings in said ordered set of marker strings, a score of each sub-string such that the score of each sub-string satisfies a matching constraint, and wherein the sum of the scores of the sub-strings is within a predetermined tolerance of a designated path score.

13. The computer program product of claim 8, wherein the method further comprises:

de-normalizing path information of each traced path.

14. The computer program product of claim 13, wherein the path information of each traced path to be de-normalized is stored in a global path array in the normalized form.

15. A computer system comprising a processor and a computer readable memory unit coupled to the processor, said memory unit containing instructions that when executed by the processor implement a method for finding a gene in a DNA sequence (S), said gene represented by an ordered set of M distinct marker strings $m_1, m_2, \ldots, m_M$, said M at least 3, said method comprising the steps of:

for $i=1, 2, \ldots, M$, identifying a sub-string $V_i$ in S, wherein sub-string $V_i$ consists of J elements $V_{ij}$ ($j=1, 2, \ldots, J$) such that $V_{ij}$ specifies a sequential position number $P_j$ in S at which $m_i$ is located in S, wherein each identical element $V_{ij}$ in $V_i$ consists of $m_i$, wherein $V_{ij}$ are ordered in sub-string $V_i$ such that $P_1 < P_2, \ldots < P_J$, wherein J is a function of i, and wherein J is at least 2 for each i;

for each sub-string $V_i$ ($i=1, 2, \ldots, M-1$), creating a plurality of directed links from specific elements of sub-string $V_i$ to specific elements of sub-string $V_{i+1}$, subject to said directed links satisfying a same inter-marker length constraint for each directed link;

tracing all paths that connect sub-string $V_1$ to sub-string $V_M$ using said directed links, wherein said paths satisfy a sequence length constraint; and storing said traced paths in a storage device of the computer system wherein said same inter-marker length constraint is selected from the group consisting of a difference between a position number within the set of specific elements of $V_i$ and a position number within the set of specific elements of $V_{i+1}$ for each directed link being a specified constant value, a difference between a position number within the set of specific elements of $V_i$ and a position number within the set of specific elements of $V_{i+1}$ for each directed link being less than a specified constant value, and a difference between a position number within the set of specific elements of $V_i$ and a position number within the set of specific elements of $V_{i+1}$ for each directed link being more than a specified constant value, and wherein each specified constant value differs from zero.

16. The computer system of claim 15, wherein said step of identifying sub-strings $V_i$ ($i=1, 2, \ldots, M$) in S includes the sub-steps of:

generating a score representative of the degree of match between the marker string $m_i$ and the sub-string $V_i$ in said DNA sequence, using a profile corresponding to said marker string; and determining that said score satisfies a predetermined constraint.

17. The computer system of claim 16, wherein said profile is representative of a grouping of strings selected from the group consisting of a set of strings that match said marker string, a set of strings that do not match said marker string, and a combination thereof.

18. The computer system of claim 15, wherein said sequence length constraint is selected from the group consisting of a minimum number of characters, a maximum number of characters, and a predetermined number of characters.

19. The computer system of claim 15, wherein the method further comprises:

recording, in a set ordered according to the occurrence of said marker strings in said ordered set of marker strings, a score of each sub-string such that the score of each sub-string satisfies a matching constraint, and wherein the sum of the scores of the sub-strings is within a predetermined tolerance of a designated path score.

20. The computer system of claim 15, wherein the method further comprises:

de-normalizing path information of each traced path.

21. The computer system of claim 20, wherein the path information of each traced path to be de-normalized is stored in a global path array in the normalized form.

* * * * *